(12) United States Patent
Baker et al.

(10) Patent No.: US 11,759,220 B2
(45) Date of Patent: Sep. 19, 2023

(54) ULTRASONIC PROBE FOR CALCULI TREATMENT

(71) Applicant: GYRUS AMCI, INC., Southborough, MA (US)

(72) Inventors: Charles Baker, Rogers, MN (US); James Macione, Ellington, CT (US); Dennis G. Lamser, Marlborough, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 466 days.

(21) Appl. No.: 17/037,072

(22) Filed: Sep. 29, 2020

(65) Prior Publication Data

US 2021/0093338 A1 Apr. 1, 2021

Related U.S. Application Data

(60) Provisional application No. 62/907,971, filed on Sep. 30, 2019.

(51) Int. Cl.
*A61B 17/22* (2006.01)
*H02N 2/00* (2006.01)
(Continued)

(52) U.S. Cl.
CPC .. *A61B 17/22004* (2013.01); *A61B 17/22031* (2013.01); *H02N 2/001* (2013.01);
(Continued)

(58) Field of Classification Search
CPC ........ A61B 17/22004; A61B 17/22031; A61B 17/22012; A61B 2017/0015;
(Continued)

(56) References Cited

U.S. PATENT DOCUMENTS

2003/0045887 A1  3/2003  Sakurai et al.
2005/0096679 A1*  5/2005  Stulen ............ A61B 17/320068
                                                        606/169
(Continued)

FOREIGN PATENT DOCUMENTS

CN      114449964 A    5/2022
DE   112020004001 T5   7/2022
(Continued)

OTHER PUBLICATIONS

"International Application Serial No. PCT/US2020/053325, International Search Report dated Dec. 14, 2020", 8 pgs.
(Continued)

*Primary Examiner* — Emily P Pham
(74) *Attorney, Agent, or Firm* — Schwegman Lundberg & Woessner, P.A.

(57) ABSTRACT

A method of treating a calculi mass can include using an ultrasonic probe to produce acoustic energy and fragment the mass. The method can include varying the frequency at which fragmentation occurs to treat the mass with a resonant frequency. The ultrasonic probe can have a distal tip for contact with the mass, where the tip has a morphology for concentrating stress on the mass. The ultrasonic probe can have two or more ultrasonic horns to allow for higher voltage and power levels.

17 Claims, 19 Drawing Sheets

(51) Int. Cl.
 *H02N 2/06* (2006.01)
 *A61B 17/00* (2006.01)
(52) U.S. Cl.
 CPC ............ *H02N 2/0075* (2013.01); *H02N 2/06* (2013.01); *A61B 2017/0015* (2013.01); *A61B 2017/00402* (2013.01); *A61B 2017/22014* (2013.01); *A61B 2017/22027* (2013.01)
(58) Field of Classification Search
 CPC .......... A61B 2017/00402; A61B 2017/22014; A61B 2017/22027; A61B 2017/00146; A61B 2017/22018; A61B 2017/320072; A61B 2217/005; H02N 2/001; H02N 2/0075; H02N 2/06
 See application file for complete search history.

(56) References Cited

U.S. PATENT DOCUMENTS

| | | | |
|---|---|---|---|
| 2005/0245823 A1* | 11/2005 | Tsuchiya | A61B 17/22012 600/439 |
| 2010/0087759 A1 | 4/2010 | Hare et al. | |
| 2014/0336665 A1 | 11/2014 | Gavala et al. | |
| 2015/0088154 A1 | 3/2015 | Vaitekunas et al. | |
| 2018/0110534 A1 | 4/2018 | Gavala et al. | |
| 2018/0263643 A1 | 9/2018 | Shelton et al. | |
| 2019/0274712 A1 | 9/2019 | Faller et al. | |

FOREIGN PATENT DOCUMENTS

| | | |
|---|---|---|
| JP | 2016529001 A | 9/2016 |
| JP | 2022549012 A | 11/2022 |
| WO | WO-2021067302 A1 | 4/2021 |

OTHER PUBLICATIONS

"International Application Serial No. PCT/US2020/053325, Written Opinion dated Dec. 14, 2020", 9 pgs.

Perkins, J P, "Power Ultrasonic Equipment—Practice and Application", Sonic Systems Ltd, [Online], Retrieved from the Internet: <URL: http://www.sonicsystems.co.uk/page/power-ultrasonics-a-guide/39/>, (2012), 11 pgs.

"Indian Application Serial No. 202247013784, First Examination Report dated Sep. 12, 2022", 7 pgs.

"Indian Application Serial No. 202247013784, Response filed Mar. 14, 2023 to First Examination Report dated Sep. 12, 2022", 19 pgs.

"International Application Serial No. PCT/US2020/053325, International Preliminary Report on Patentability dated Apr. 14, 2022", 11 pgs.

"Japanese Application Serial No. 2022-519580, Notification of Reasons for Refusal dated Apr. 4, 2023", w/ English Translation, 7 pgs.

* cited by examiner

ULTRASONIC PROBE FOR CALCULI TREATMENT

CROSS-REFERENCE TO RELATED APPLICATION

This application claims the benefit of priority to U.S. Provisional Patent Application Ser. No. 62/907,971, filed on Sep. 30, 2019, the contents of which are incorporated herein in their entirety.

TECHNICAL FIELD

The present document relates to techniques for breaking obstructions, such as physiological "calculi" using lithotripsy, and example an ultrasonic probe.

BACKGROUND

Medical endoscopes were first developed in the early 1800s and have been used to inspect inside the body. A typical endoscope has a distal end comprising an optical or electronic imaging system and a proximal end with controls such as for manipulating the device or for viewing the image. An elongate shaft connects the proximal and distal ends. Some endoscopes allow a physician to pass a tool down one or more working channels, for example, to resect tissue or retrieve objects.

Over the past several decades, several advances have been made in the field of endoscopy, and in particular relating to the breaking up of physiologic calculi in the bile ducts, urinary tract, kidneys, and gall bladder. Physiological calculi in these regions may block ducts and cause a patient a substantial amount of pain and therefore is broken down and/or removed. Different techniques have been developed to break up calculi, including ultrasonic or other acoustic lithotripsy, pneumatic lithotripsy, electro-hydraulic lithotripsy (EHL), and laser lithotripsy such as can include breaking up of calculi using a green light, YAG, or holmium laser.

SUMMARY OF THE DISCLOSURE

The present disclosure provides, among other things, devices and methods for calculi fracture and removal using an ultrasonic probe. During treatment, drive signals can be mixed to treat the calculi mass. The ultrasonic probe can include a probe tip with a morphology correlated to the targeted calculi mass type or size. The ultrasonic probe can include two or more ultrasonic horns to aid probe performance.

During calculi treatment, one or more drive signals can be transmitted to an ultrasonic transducer within the probe. The transducer can vibrate a shaft (e.g., a waveguide) of the probe based on the drive signals transmitted to the transducer. In sonic cases, the drive signals can be provided in two or more varying frequencies. The use of several varying frequencies can allow for a sweep around several frequencies, such as to find the resonant frequency of the targeted calculi and allow more efficient breakup of that calculi mass.

The ultrasonic probe can have a probe tip with a morphology designed for treating the targeted calculi mass. For example, the probe tip can have a tip with reduced area and more concentrated corners for treatment of a harder calculi mass. In contrast, the probe tip can be flatter for treatment of a softer calculi mass.

Two or more ultrasonic horns can be used in the ultrasonic probe, such as in the transducer and in the waveguide. The ultrasonic horns can be placed relative to one or more stress nodes within the waveform to allow for a probe able to withstand higher voltage or power levels.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Devices and techniques as described herein may be used in regard to an ultrasonic probe, such as for use with a nephroscope or trocar. Features may be used with an ultrasound lithotripter device to create technologies which allow for faster target removal, such as calculi removal. Evaluation of faster mass removal rates for a calculi can show that large forces are needed. For example, it has been found that higher driving voltages/power levels, which produce higher displacements of the probe tip, are more effective in accelerating mass removal time. However, use at higher driving voltages/power levels is that the stress from pushing the probe this hard can cause the probe to break within minutes or even seconds. With features as described herein, this issue of a probe breaking when using higher driving voltages/power levels may be addressed by providing the probe with a probe tip horn at a distal end of the probe. Providing a probe tip horn allows the probe to run at higher displacements (with use of higher driving voltages/power levels) without the probe breaking. This can be used with sinusoid waveforms or generally square waveforms.

Figure 1:
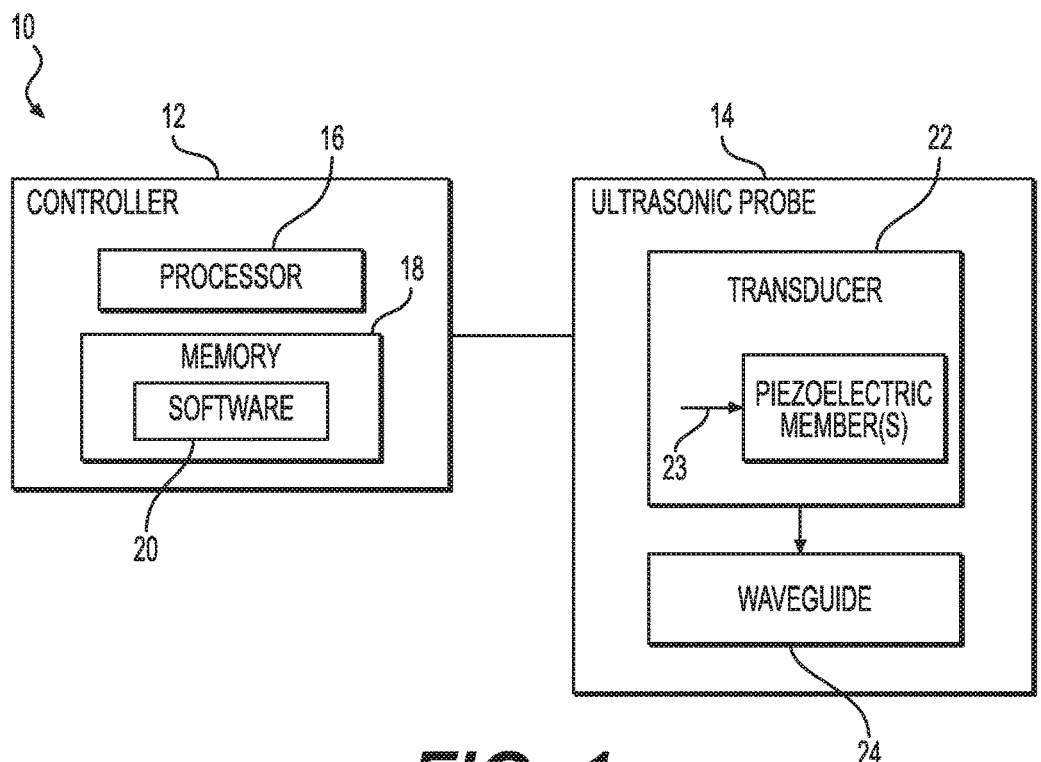
FIG. 1 illustrates a schematic diagram of an example apparatus incorporating features of an ultrasonic probe.
Figure 2:
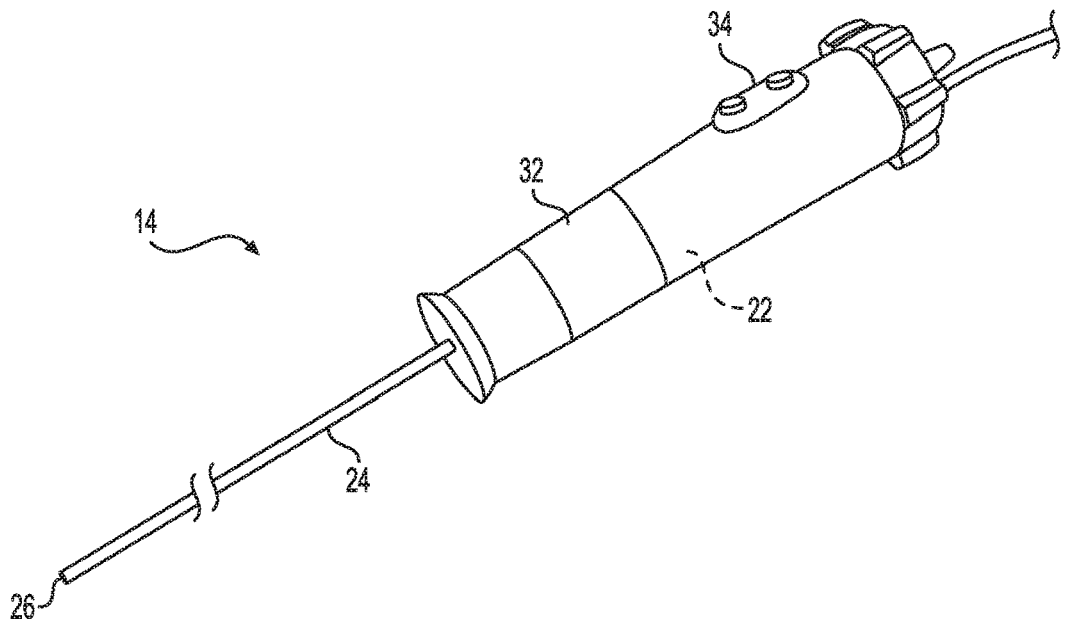
FIG. 2 illustrates a perspective view of an example ultrasonic probe.

Referring to FIG. 1 and FIG. 2, there is shown a schematic diagram of a system 10 for use with an example probe 14. Although the features will be described with reference to the examples shown in the drawings, it should be understood that features can be embodied in many alternate forms of examples. In addition, any suitable size, shape or type of elements or materials could be used.

The system 10 can include a controller 12 and an ultrasonic probe 14. In an example, the system 10 is a medical system, such as for lithotripsy. The controller 12 can include at least one processor 16 and at least one memory 18 with software 20. The ultrasonic probe 14, such as shown in FIG. 2, can include a transducer 22 and a shaft as a waveguide 24. The controller 12 can include a driver, or control a driver, to send drive signals to the transducer 22. The transducer 22 can include one or more piezoelectric members 23, such as a stack, as illustrated in FIG. 1. Here, the piezoelectric members 23 can be configured to receive a drive signal via the controller 12 to actuate the transducer. The waveguide 24 can be configured to be moved or vibrated by the transducer 22.

Figure 3:
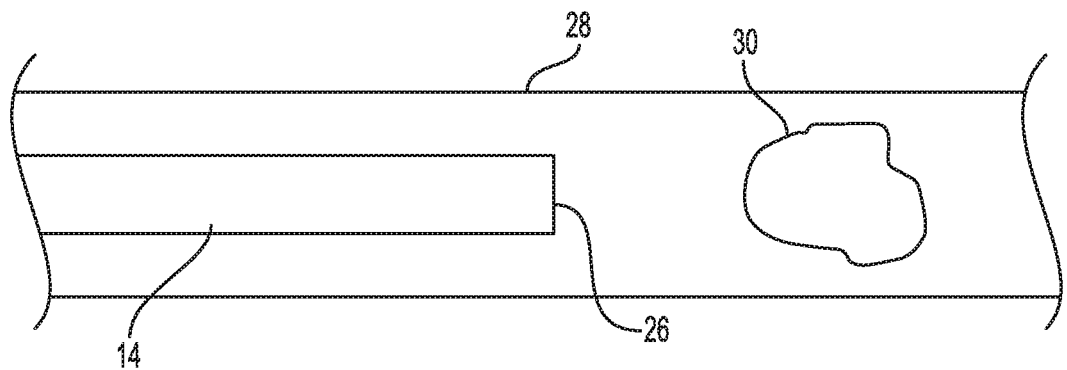
FIG. 3 illustrates a close-up view of an example distal tip of the ultrasonic probe of FIG. 2.

FIG. 3 illustrates the distal tip 26 of the probe 14. As illustrated with FIG. 3, the distal tip 26 of the waveguide 24 may be inserted into a patient 28 into contact with a target 30, such as a calculi, to allow the probe 14 to use ultrasonic waves to fracture the target 30. In this example, the probe 14 can include a handle section 32 for the user. The handle section 32 can include a user control 34. The transducer 22 can be located in the handle section 32. The waveguide 24 can extend forward in a general cantilever fashion from the distal end of the handle section 32.

Figure 4:
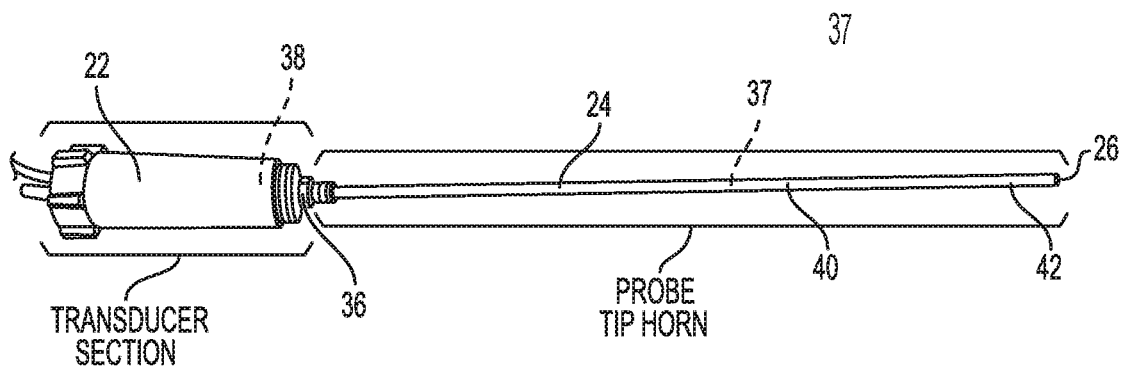
FIG. 4 illustrates a side view of the example ultrasonic probe of FIG. 2.
Figure 5:
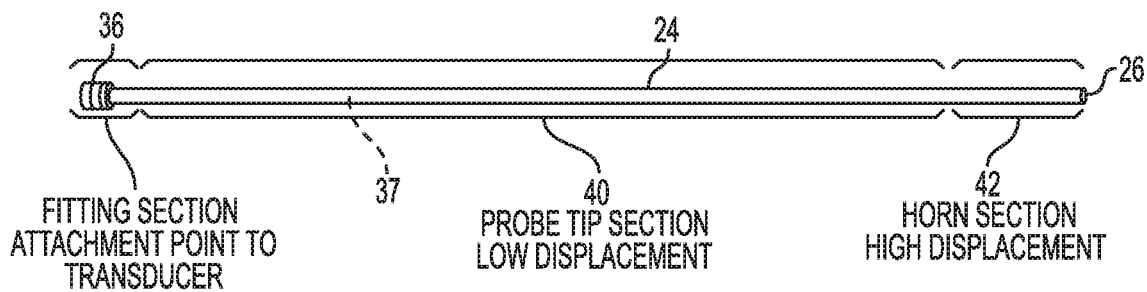
FIG. 5 illustrates a close-up view of an example waveguide of the ultrasonic probe of FIG. 4.
Figure 6:
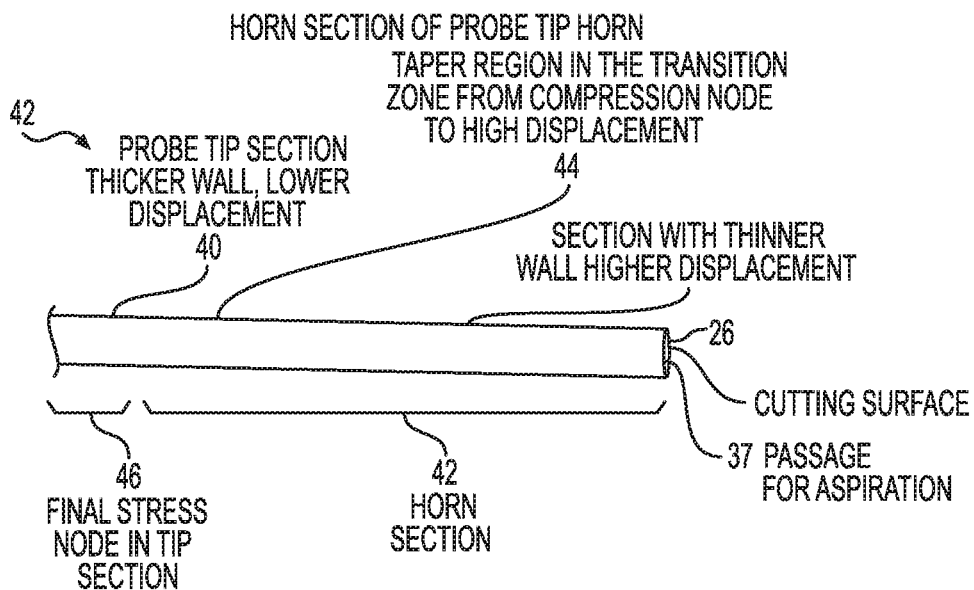
FIG. 6 illustrates a close-up view of an example distal tip of the ultrasonic probe of FIG. 4.

FIGS. 4-6 show additional views of the probe 14. Referring to FIGS. 4-6, a fitting section or connector 36 is provided at the proximal end of the waveguide 24 to connect the waveguide to the transducer section having the transducer 22. The transducer section can include a first horn 38. The first horn 38 can be part of the transducer 22 and the proximal end of the waveguide 24. The waveguide 24 can include a probe tip section 40 and a distal horn section 42. Thus, two horns are provided; the first horn 38 located as part of the transducer 22 and the second horn 42 located proximate the distal end or tip 26 of the probe. In some cases, more than two horns could be provided. In addition, in another alternate example, only a single horn might be provided; the horn 42. The probe tip section 40 can be configured to have sections with a first level of displacement, and the distal horn section 42 can be configured to have a different second level of displacement. In the example shown, the second level of displacement is relatively higher than the first level of displacement. The distal end 26 of the probe forms a cutting surface for direct contact with the target 30. The waveguide 24 can also include a passage or conduit 37 for aspiration from the distal end 26 into the handle section 32. By providing a horn at the distal end of the probe, such as beyond a final stress node for example, the probe can provide a displacement at the distal cutting edge 26 which is higher than a convention probe, but with a reduced risk that the probe will break based upon the higher displacement.

As seen in FIG. 6, the probe tip horn can include a transition zone 44 between the probe tip section 40 and the distal horn section 42. The transition zone 44 can be located after the distal, final stress node 46 as further discussed below. The transition zone 44 can provide a taper region from the final stress node 46 to a location of the second relatively higher displacement for the waveguide 24 at the distal horn section 42.

Figure 7A:
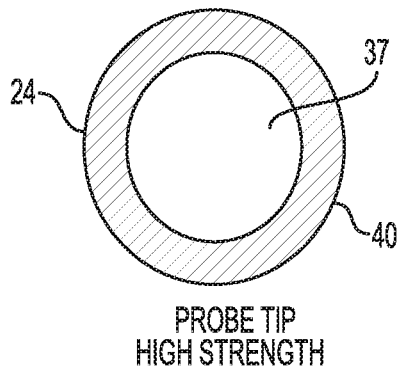
FIGS. 7A-7B illustrates schematic diagrams of an example distal tip of an ultrasonic probe.
Figure 7B:
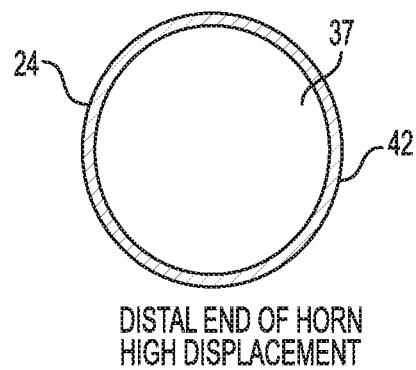

FIGS. 7A and 7B illustrate close-up views of a probe tip and horn. In FIGS. 7A and 7B, the waveguide 24 has a generally non-uniform wall thickness. FIG. 7A illustrates a cross section of the waveguide at the probe tip section 40 and FIG. 7B is a cross section of the waveguide at the distal horn section 42. As can be seen, with this example the wall thickness is smaller at the distal horn section 42 relative to the probe tip section 40. Thus, the passage 37 may be larger at the distal horn section 42 than at the probe tip section 40. The transition zone 44 provides a taper between these two sections to form the functionality of the horn.

Figure 8:
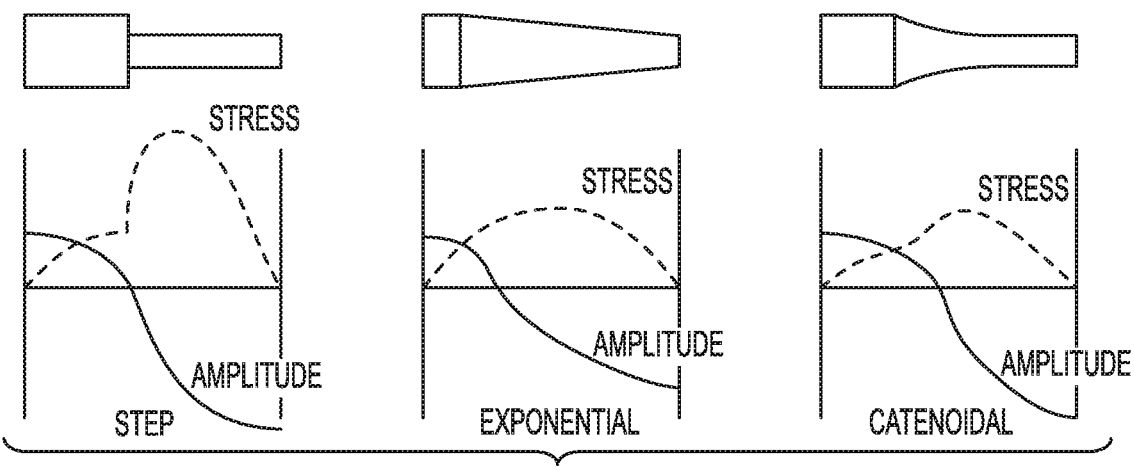
FIG. 8 illustrates side views of example distal tips and associated waveforms for an ultrasonic probe.
Figure 9:
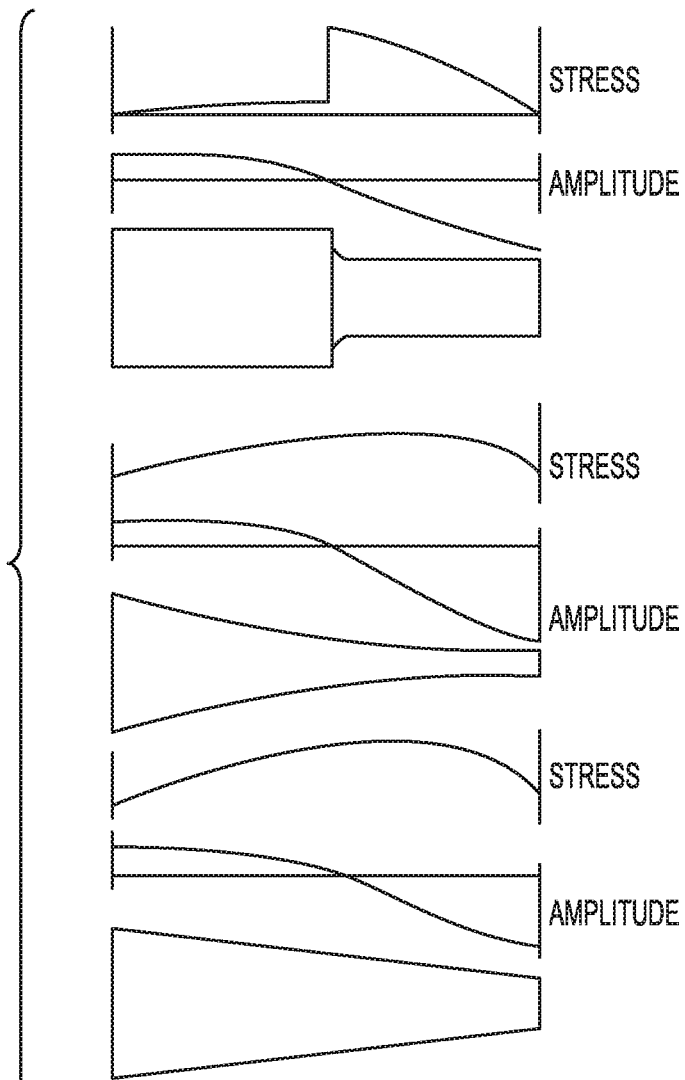
FIG. 9 illustrates side views of example distal tips and associated waveforms for an ultrasonic probe.

The horns 38, 42 (ultrasonic horns) are a way of creating increase amplitude of displacements from the ultrasound transducer. This is done by changing the cross sectional area of the base of the horn to the tip of the horn. The gain of the horn, if lossless, is the ratio of the surface area at the base to that at the tip. The horn gain applies to displacement of the mechanical waves. The shape of the horn can determine the horn's gain. This is because of the effect of displacement nodes. The horn(s) may be designed as long a resonant bar with a half wavelength. By changing the shape of a horn, it is possible to give the horn a gain factor; increasing the amplitude of the vibration. Examples horns are illustrated in FIGS. 8 and 9. Three common horn designs are step, exponential and catenoidal as shown in FIG. 8 (Ultrasonic Welding. Handbook of Plastics Joining (Second Edition). A Practical Guide. 2009, Pages 15-35; https://www.sciencedirect.com/science/article/pii/B9780815515814500044). A catenoidal horn has the highest amplitude gain and limited stress. Further amplitude and stress curves are shown in FIG. 9 for other examples (Power Ultrasonic Equipment—Practice and Application http://www.sonicsystems.co.uk/page/power-ultrasonics-a-guide/39/).

Figure 10:
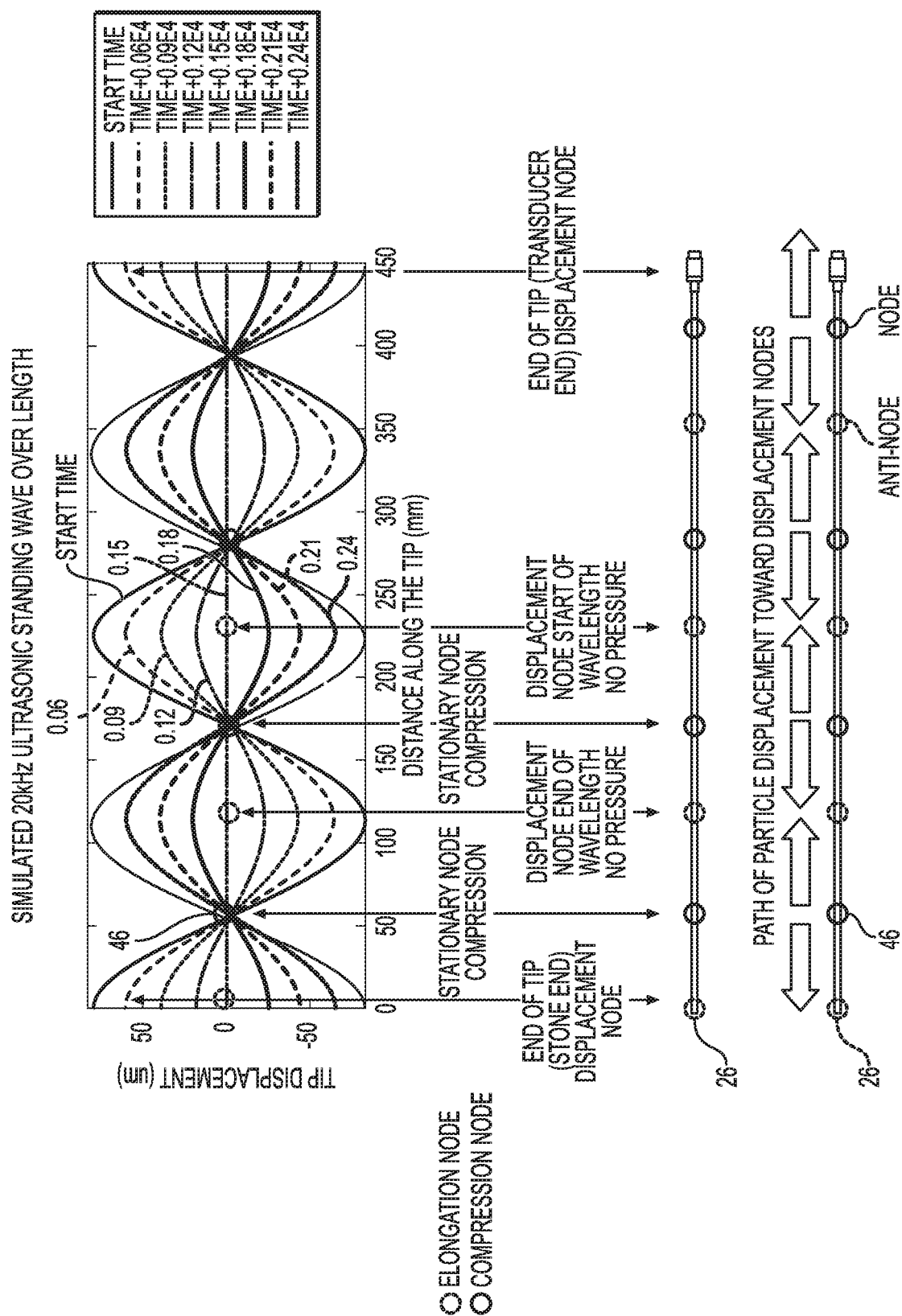
FIG. 10 illustrates a chart depicting an example of node and anti-node placement in an ultrasonic probe.

In FIG. 10, a diagram is shown illustrating displacement along the length of the waveguide 24 for a simulated 20 kHz standing wave. As can be seen, there are nodes (also called compression nodes or stationary notes or stress nodes) having compression or tension with no displacement (ideally). Also as shown in FIG. 10, there are antinodes (also called displacement nodes or elongation nodes). The antinodes are configured to have displacement or elongation. The locations of the stationary nodes are locations of stress where failure might occur. The transition zone 44 is located after the last stationary node 46.

In this example, the example probe tip horn is composed of three main sections; two of which are shown in FIG. 6. The first section is the probe tip section 40 which will provide a cross sectional area over all the stress nodes shown in FIG. 10 which is relatively larger than the cross sectional area of the other two main sections. The relatively large cross sectional area along the probe tip section 40 can help to protect this area from failure. The distal horn 42, on average over its length, has a cross sectional area which is thinner than the cross sectional area of the probe tip section 40. This relatively thinner cross sectional area can be configured to exhibit large displacements in response to the same forces passing through the probe tip body. The transition 44 between the distal horn 42 and the probe tip section 40 has a taper between the two cross sectional areas which can be derived from any decreasing mathematical function or even a single step from one inner diameter to another. The taper or overlap of the two sections will decrease stress at the start or base of the horn 42. In this example, the transition 44 provides an incremental change or gradual transition in area because the stress is still present in areas adjacent to the stress node 46 and not just located at the center of the stress node 46. The position of the start of the horn section and taper is at or near the final stress node 46 in the probe tip section 40. This allows areas with peak stress to have a large cross sectional wall area over them. The length of the horn of the probe tip horn is around ¼ to ½ wavelength of the fundamental frequency. The longer the horn is with respect to the final displacement node allows (ending at tip 26) more overall displacement to occur. The passageway 37 within the center of the horn 42 provides for aspiration to remove fragments of the calculi or particulate being removed. The tip 26 of the horn is a cutting surface. Features as described herein provide both a cutting surface and is hollow with an entrance into an aspiration passage at the distal end of the probe. The target material 30 may be calculi which may have varying hardness for example.

The waveguide 24 can have an attachment point 36 for connection with the transducer 22. The waveguide 24 may have an attachment point for a spring and free mass (not shown). However, the waveguide 24 may function without the spring. The probe tip section 40 has a length many times longer than the horn 42, allowing passage/location of low stress areas of the probe tip section through the device and into the patient's body. This may cover more than one stress node over length.

The ratio of the cross sectional areas of the probe tip section 40 (see FIG. 7A) to that of the horn section 42 (see FIG. 7B) can be relatively larger. This allows for large displacements to occur in the horn 42 with respect to the rest of the probe tip body. The cross section of the horn 42 may be reduced in either the outer diameter, the inner diameter, or in combination of the outer diameter and the inner diameter with respect to the rest of the probe tip body. The horn 42 does not need to have a same inner diameter or a same outer diameter as the probe tip section 40. The relative mechanical displacement gain of the probe tip 26 is given by the ratio of the cross sectional area of the that probe tip (APT) to the horn (AH) as Gain: APT/AH. The larger cross sectional area in the probe tip section 40 makes it stronger and protects it from damage in stress nodes while the thinner cross section in the horn section 42 allows it to have larger displacements at the distal tip 26. With the example shown in FIGS. 4-7, by providing a horn at the distal end of the probe, beyond the final stress node, the probe can provide an increased displacement at the distal cutting edge 26 with reduced risk that the probe will break based upon the increased displacement. The probe would otherwise be more likely to break if the second horn was located before the last stress node.

Figure 11:
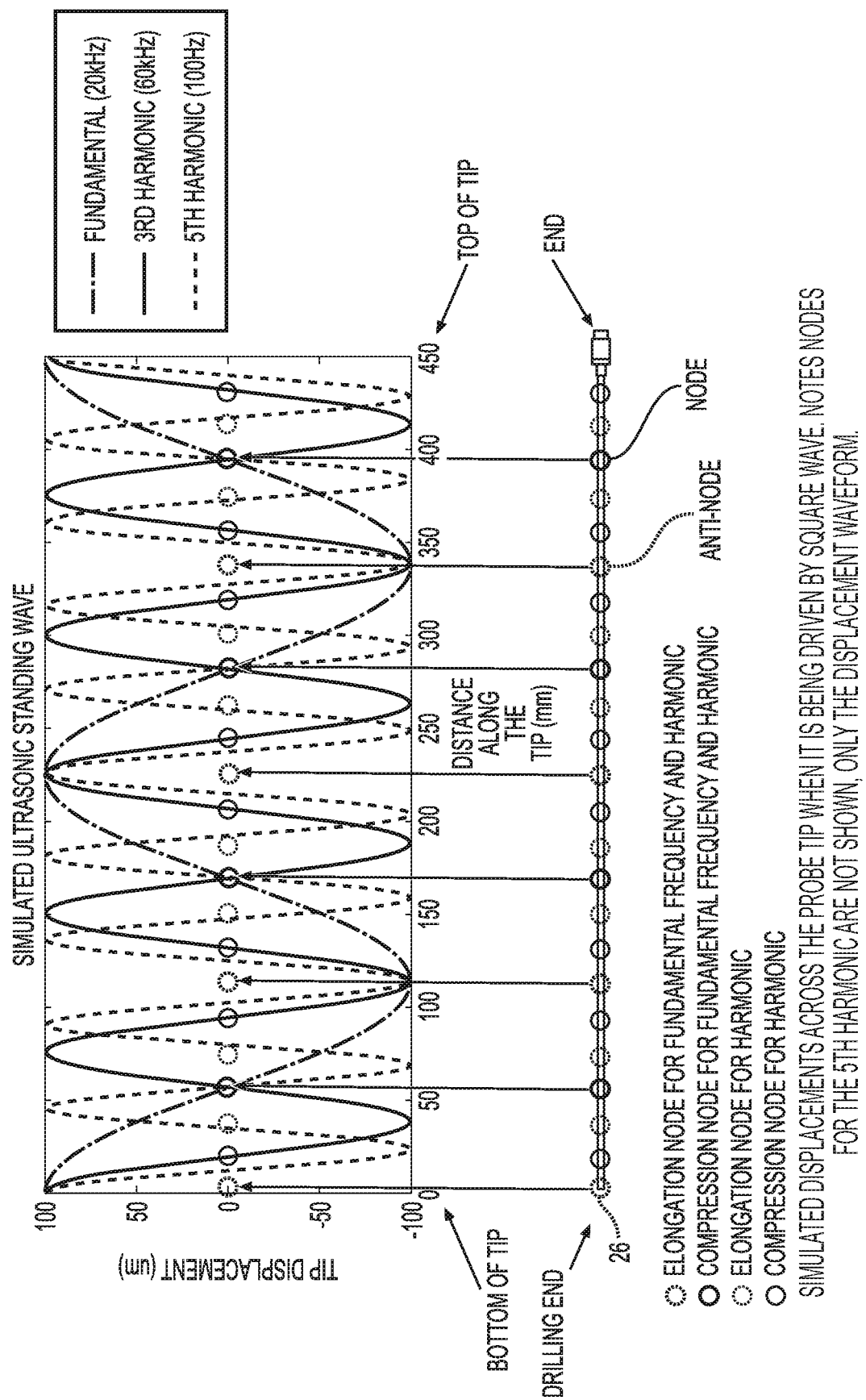
FIG. 11 illustrates a chart depicting an example of node and anti-node placement in an ultrasonic probe.
Figure 12:
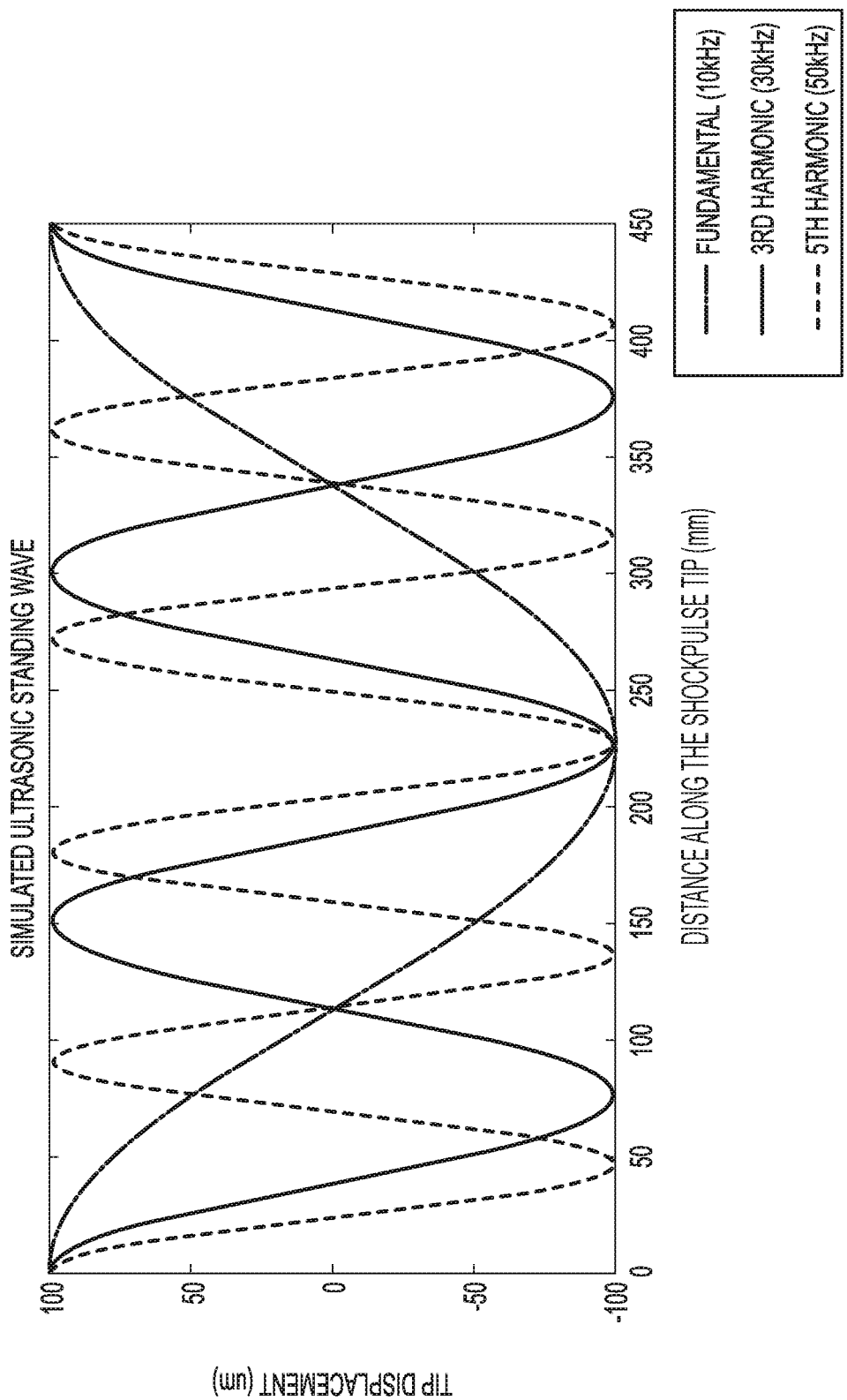
FIG. 12 illustrates a chart depicting an example of a waveform in an ultrasonic probe.

As noted above, features as described herein may be used with sinusoid waveforms or generally square waveforms for example. Referring also to FIG. 11 simulated displacement across the probe tip is shown when being driven by a wave approximating a square wave, and shows a fundamental frequency of 20 kHz, a 3rd harmonic (60 kHz) and a 5th harmonic (100 kHz). Nodes (static nodes) and anti-nodes (displacement nodes) are shown. Please note that in FIG. 11 nodes for the 5th harmonic are not shown; only the displacement waveform for the 5th harmonic is shown. FIG. 12 shows a similar diagram for a fundamental frequency of 10 kHz, 3rd harmonic (30 kHz) and 5th harmonic (50 kHz). This shows that there are alternative harmonic driving opportunities for driving the transducer at different frequencies to increase the length of the displacement node while allowing the harmonics to have higher impact repetition. The use of harmonic energy in a multiple of a fundamental wavelength, allows super-position of displacement at the tip of the transducer with the harmonic energy as a multiple of the fundamental wavelength (wavenumber).

An ultrasonic transducer converts electrical energy to mechanical waves through the piezoelectric effect. Thus, the transducer in this example comprises a piezoelectric member. The piezoelectric effect is the transduction mechanism with an increase in the mechanical length of the transducer in response to a voltage on the transducer. The change in length of the transducer is proportional to many variables including, but not limited to, the voltage level and the frequency in which the signal is applied to the transducer.

When the electrical frequency applied to the transducer is equal to the time for the mechanical wave to traverse the crystal and return, optimal energy conversion may occur due to resonance and can create a mechanical displacement that is many times larger than at any other frequencies.

Figure 13A:
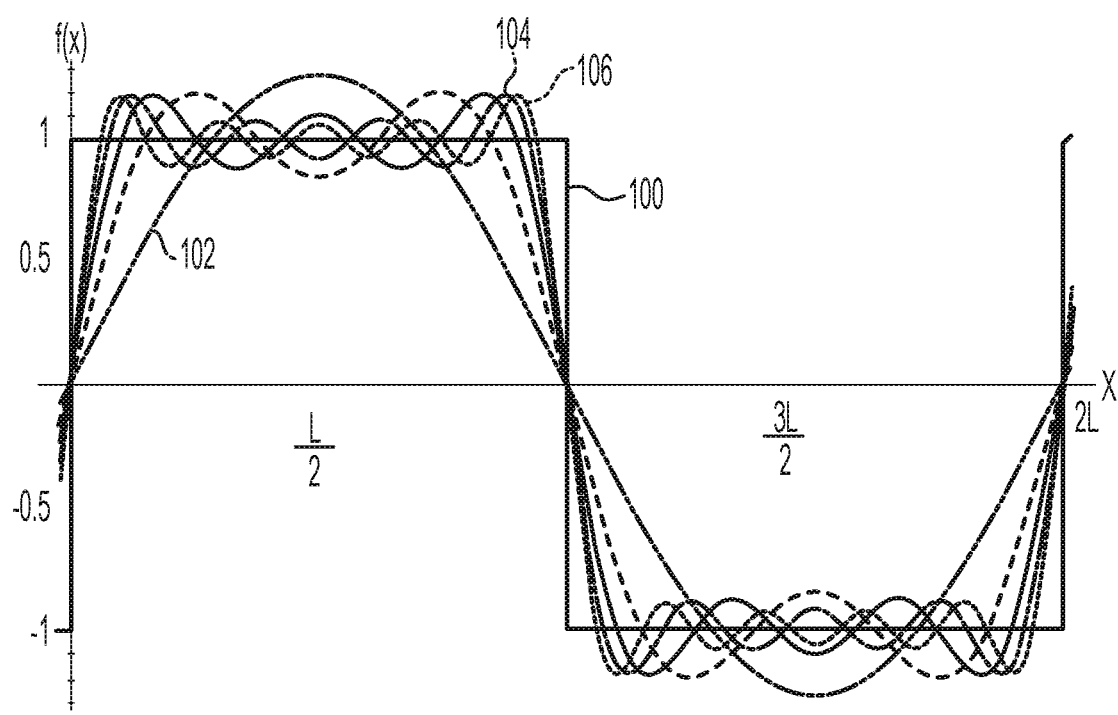
FIGS. 13A-13E illustrates examples of waveforms in an ultrasonic probe.

With reference to FIG. 13A, the wave 100 represents a Square Wave, the wave 102 is the first fundamental sine wave, the wave 104 is the first harmonic and the wave 106 is the 2nd harmonic. In this manner, the signals to create the mechanical harmonics are comprised in the same electrical wave being used to excite the piezoelectric crystal. In one example, the input signal is a summation of a plurality of sinusoidal waveforms; each sinusoidal waveform being of a different frequency. The frequency of each sinusoidal waveform may be related to (e.g., harmonic of) a particular sinusoidal frequency. In another example, the input signal may include a wave at one or more frequencies related to a fundamental frequency of the piezoelectric stack. The input may include a signal whose frequency varies during processing. The input may include a signal that approximates a square wave. A square wave is merely an infinite summation of sine waves of fundamental, first, second, third, . . . nth harmonic. One may not be able to accomplish an infinite sum or a perfect square-shape (see the bumps 110 near the edge of the square shape in FIG. 13B in a digital signal), but the signal may generally approximate a square wave. FIGS. 13C-13E show the individual waves 102, 104, 108 of FIG. 13B separately for clarity.

In response to the input waveform of FIG. 13A, the mechanical states of the transducer may approach a ballistic like impact s. The system may input multiple frequencies into the waveguide, which will include the resonant frequency, for use in breaking a target. The multiple frequencies may be provided with any waveform. Use of an approximate square wave is merely one example. Any suitable waveform(s) with a variable frequency or multiple frequencies, one of which will induce resonance in a target, may be used. Use of multiple frequencies is more likely to excite a target's resonant frequency to allow self-resonance. Use of a square wave (or wave approximating a square wave), with faster transition in the transducer (piezoelectric driver), can also provide an increased acceleration of displacement in the waveguide versus a conventional acceleration of displacement, and an increased velocity of displacement in the waveguide versus a conventional velocity of displacement.

The use of a driving system with a plurality of frequencies (fundamental and/or one or more harmonics) allows more overall energy and power to get into the transducer and, thus, create more energy at the probe tip. The system being described is capable of aspiration in order to remove parts of a target, such as parts of a stone, which have been removed from a main target body. Although the system is described as working from the fundamental frequency, the electrical ultrasound driver may be altered so that the fundamental frequency becomes what was originally a harmonic or even a subharmonic, allowing a new range of frequency combinations to be used. So, for example, if the primary system is designed to work at 20 kHz, the fundamental frequency can be changed to 60 kHz or 10 kHz with the 3rd harmonics in new positions.

Figure 13B:
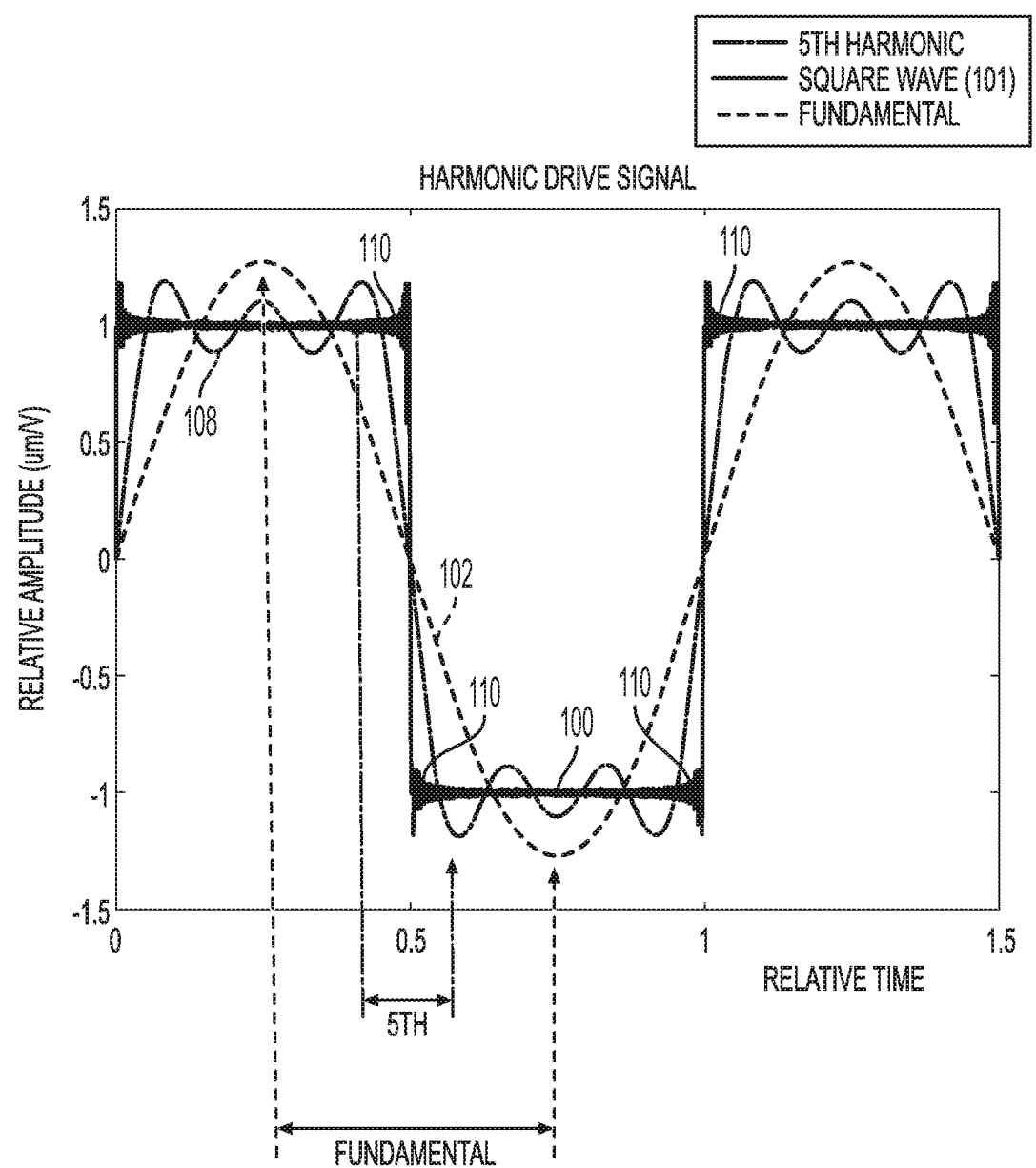
Figure 13C:
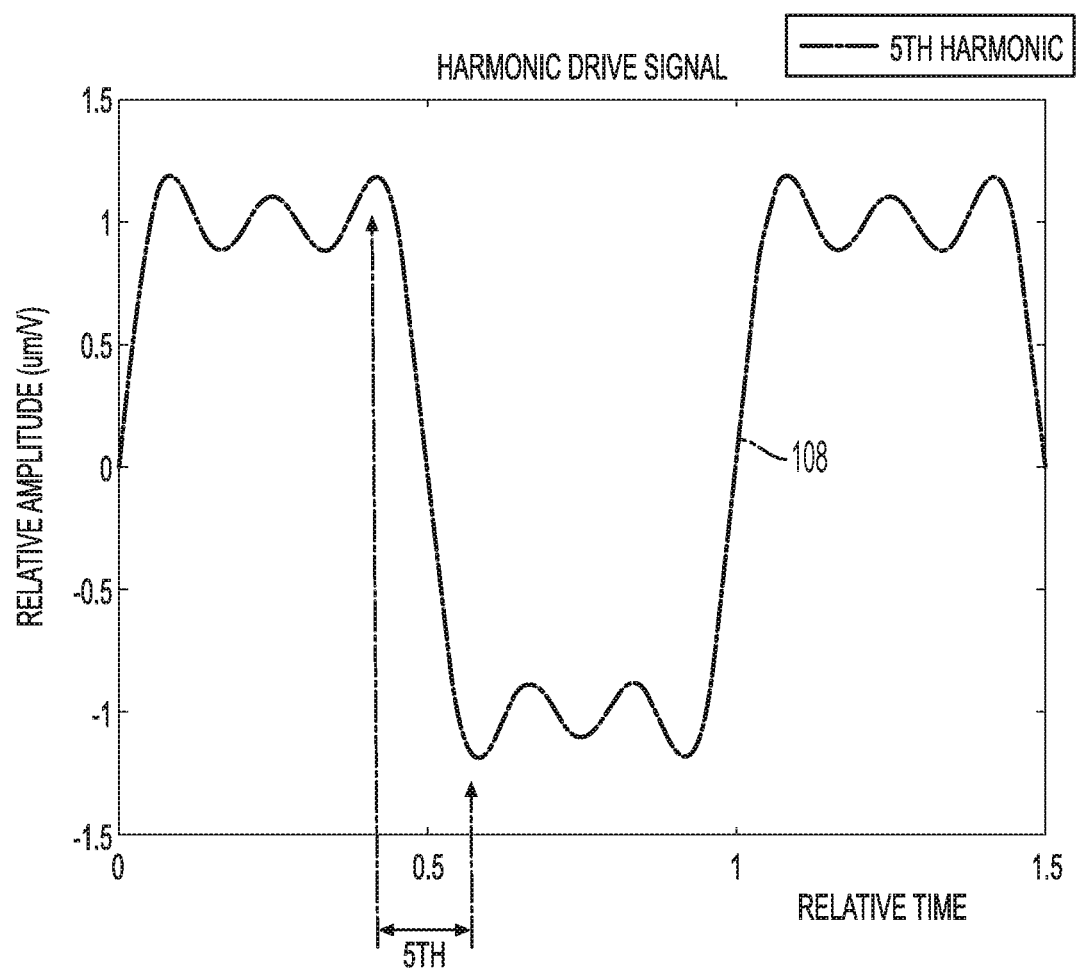
Figure 13D:
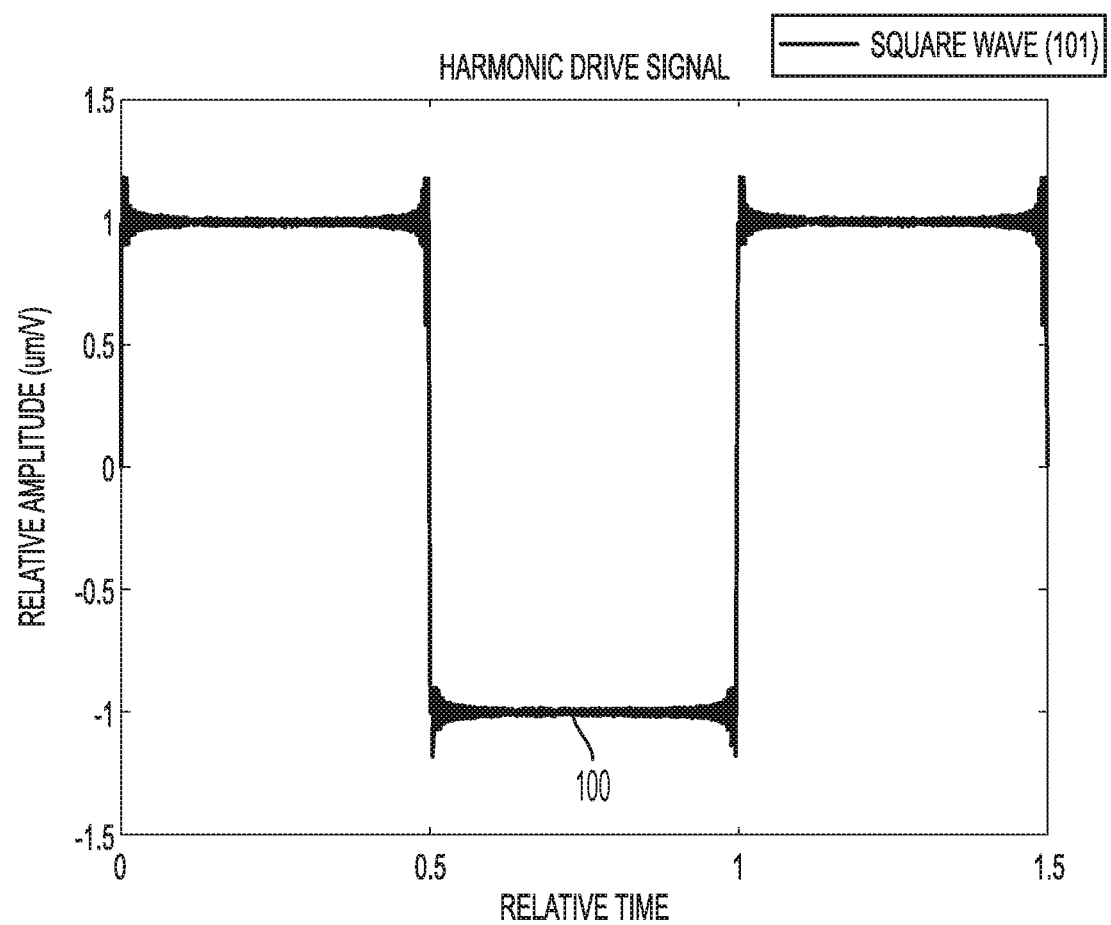
Figure 13E:
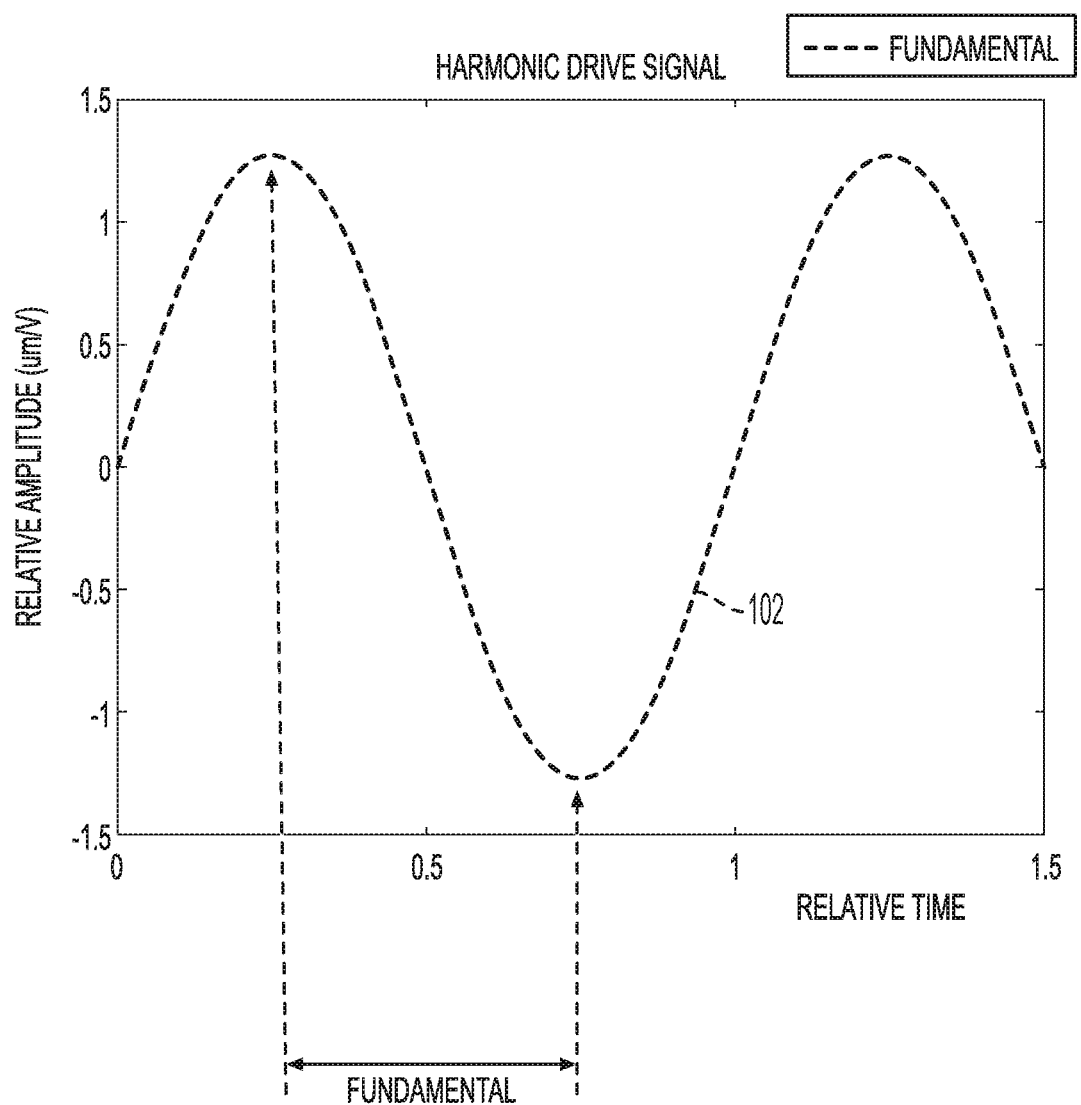

FIG. 13B shows a transition of the fundamental frequency, 5th harmonic, and an approximated square wave (from 101st harmonic) having different transition times, with the approximated square wave being almost instantaneous. It is believed that the mass removal will be improved with faster displacement transition times per unit time. Also expected is a higher displacement output although this is not shown in the figure.

Figure 14:
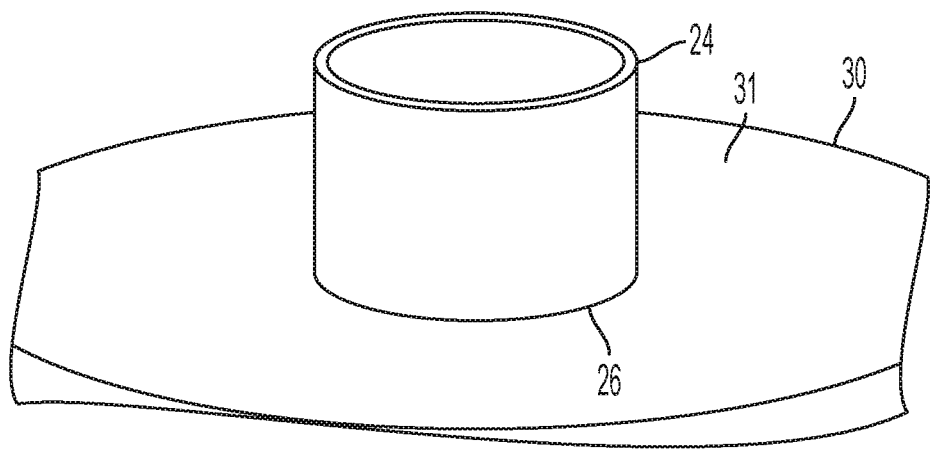
FIG. 14 illustrates a schematic view of an example probe tip for an ultrasonic probe.
Figure 15:
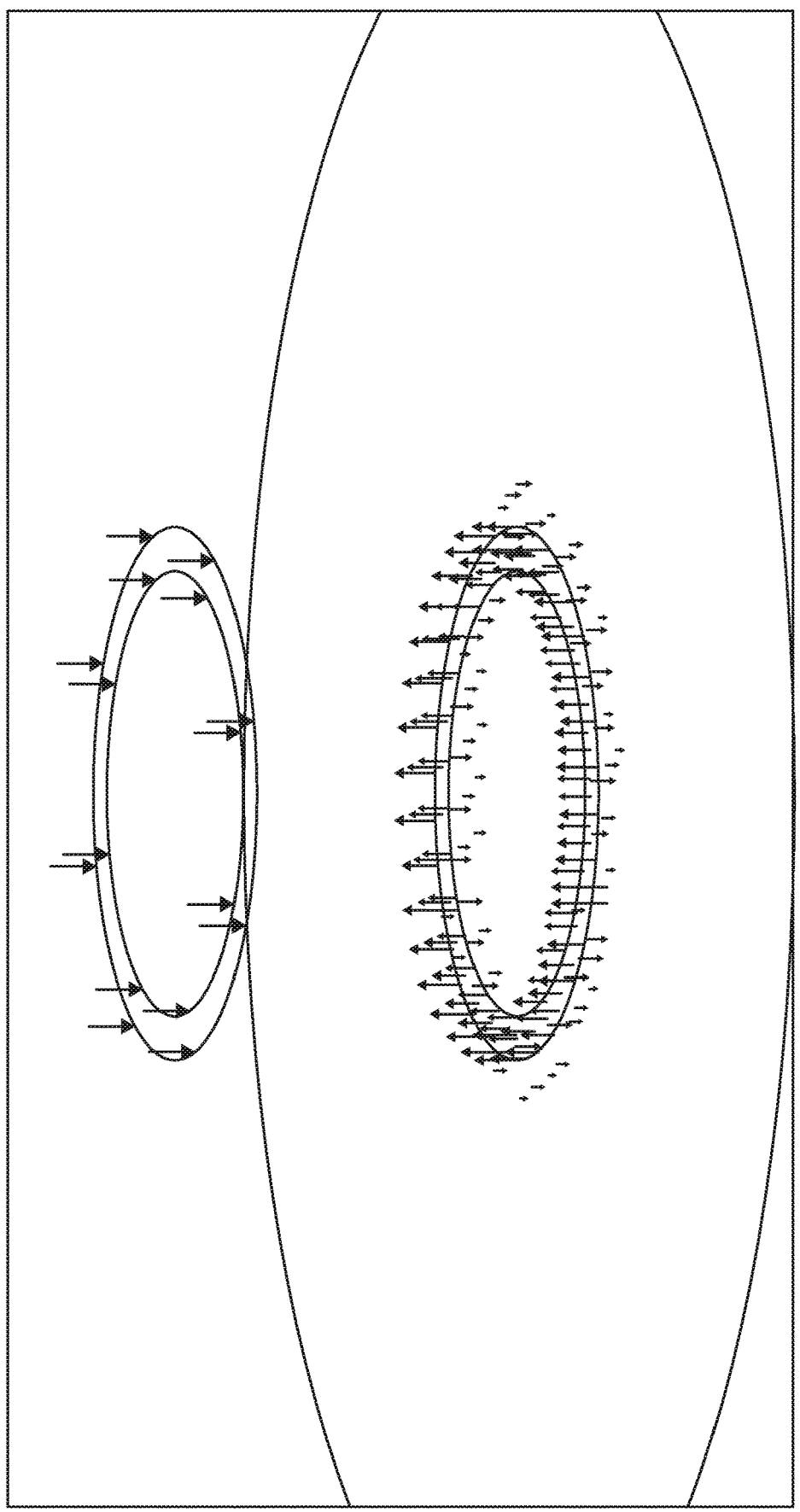
FIG. 15 illustrates a schematic view of an example probe tip for an ultrasonic probe.
Figure 16:
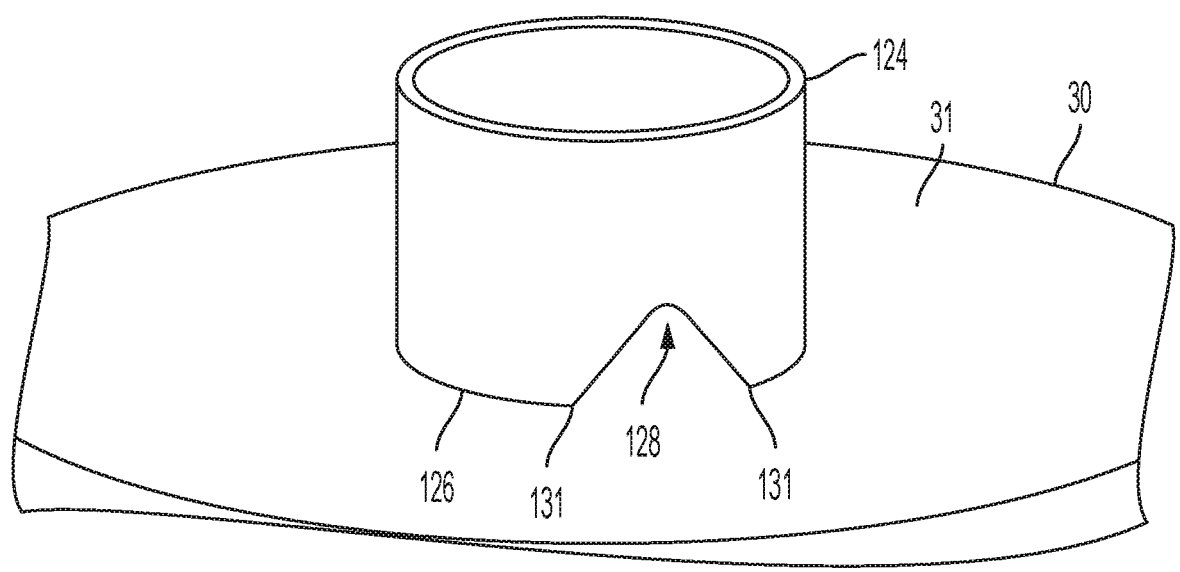
FIG. 16 illustrates a schematic view of an example probe tip for an ultrasonic probe.
Figure 17:
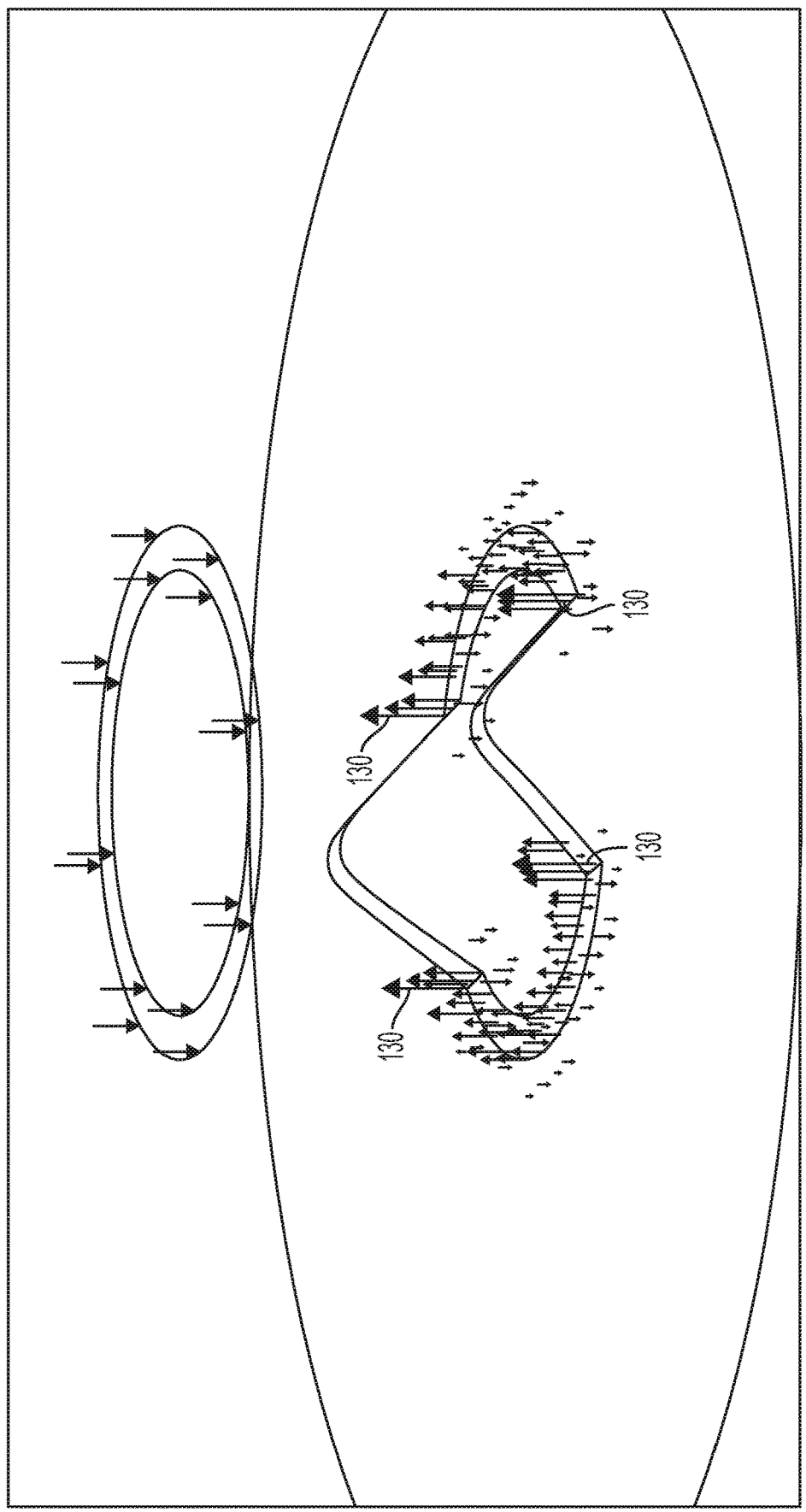
FIG. 17 illustrates a schematic view of an example probe tip for an ultrasonic probe.
Figure 18:
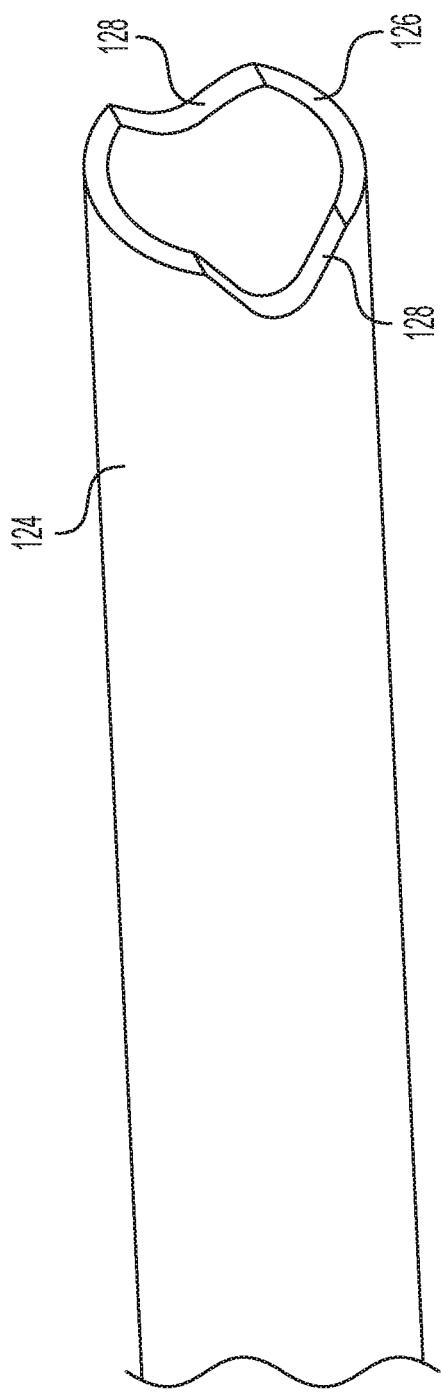
FIG. 18 illustrates a schematic view of an example probe tip for an ultrasonic probe.

Another feature is to drive the transducer at an even harmonics of the fundamental frequency. So, for example, for a system whose fundamental frequency is at 20 kHz, the transducer may be driven at 40 kHz. Another example is the transducer being driven at 10 kHz, or other multiples of the fundamental frequency (e.g., at 30 kHZ, etc.). Referring also to FIG. 14, the distal tip 26 is shown against the surface 31 of a target 30. In this example, the distal tip 26 is generally flat. FIG. 15 shows a diagram illustrating tip contact pressures against the surface 31. Referring also to FIGS. 16 and 17, similar diagrams are shown in regard to a different distal tip 126 of a shaft forming a waveguide 124, such as the distal tip of the shaft shown in FIG. 18 for example. The distal tip 126 forms a leading surface of the shaft. In this example the tip 126 comprises recesses 128 into the leading edge of the tip 126. The recesses 128 have a general wedge or triangular shape, but other shapes could be provided. The larger arrows in FIG. 17 illustrate larger pressures. As seen in FIG. 17, the diagram illustrating tip contact pressures against the surface 31 shows areas 130 of increased pressure. The reduced area at the leading edge because of the recesses 128, assuming a same force is applied, causes an increase in contact pressure. These areas 130 are at the corners or junctions 131 of the recesses 128 with the generally flat leading edge of the distal tip. The corners have a general wedge shape, but with a curved radius. Thus, each recess 128 terminates in a leading edge at 131; with the leading edge forming a non-zero angle with the generally flat leading surface 126. In this example the recesses 128 are located diametrically opposed to each other.

Figure 19A:
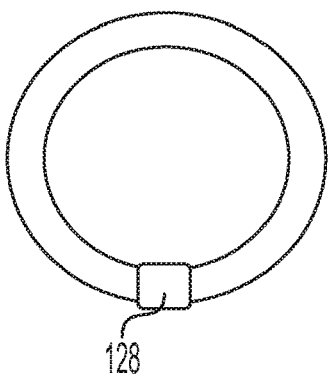
FIG. 19A-19J illustrate schematic views of example probe tips for an ultrasonic probe.
Figure 19B:
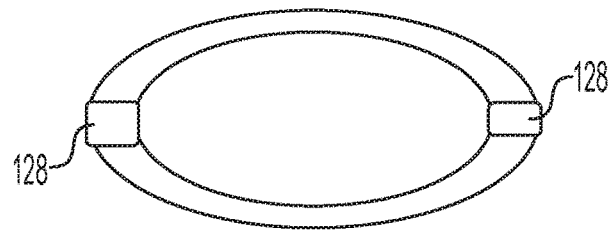
Figure 19C:
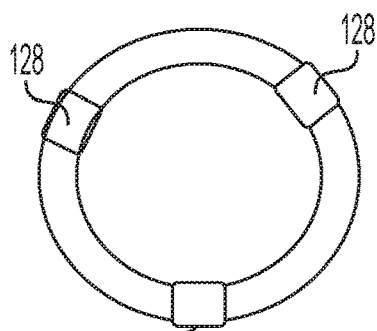
Figure 19D:
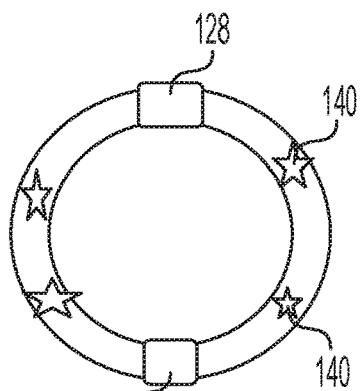
Figure 19E:
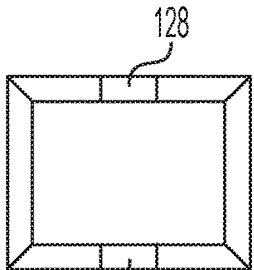
Figure 19F:
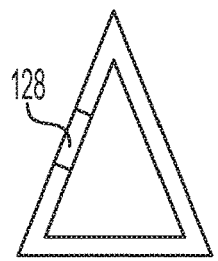
Figure 19G:
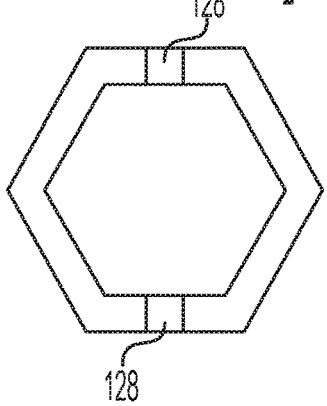
Figure 19H:
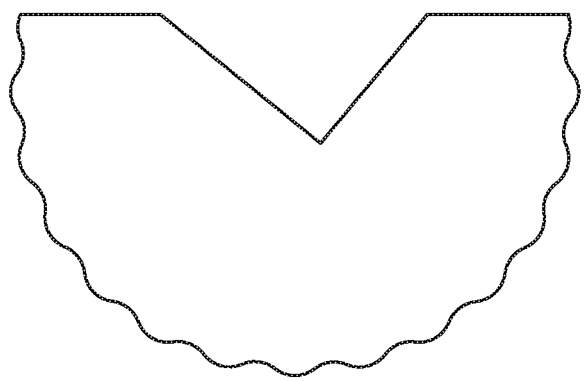
Figure 19I:
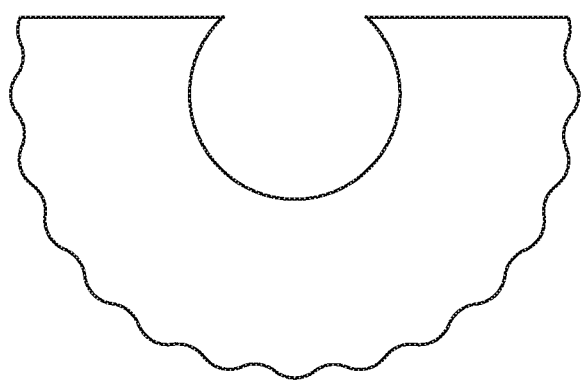
Figure 19J:
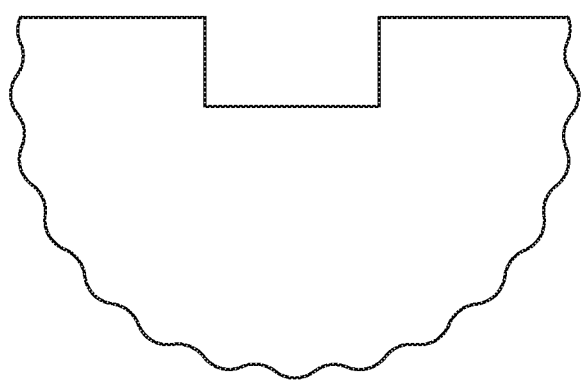

Referring also to FIGS. 19A-19G, other shapes at the distal tip of the shaft could be provided including, for example, having only one recess as shown in FIG. 19A, having an oval or non-circular shape as shown in FIG. 19B, having more than two recesses 128 and not diametrically opposed as shown in FIG. 19C, having additional teeth 140 as shown in FIG. 19D, having a square or rectangular shape as shown in FIG. 19E, having a triangular shape as shown in FIG. 19F and having a polygon shape as shown in FIG. 19G. Referring also to FIGS. 19H-19J, other shapes of the recesses 128 could be provided, such as, for example, V shaped with relatively sharp angles as shown in FIG. 19H, circular shaped as shown in FIG. 19I, and rectangular or square shaped as shown in FIG. 19J. These are merely examples and should not be considered as limiting.

With features as described herein, an ultrasonic lithotripsy probe may be provided to have concentrated tip contact pressures on a target, such as a calculi for example. This concentration of tip contact pressure will aid in the fragmentation of the target, especially for a hard calculi burden for example. Although the example shown in FIG. 18 has two generally semi-circular shapes as a flat surface leading end and two triangular shaped recesses, other shapes could be provided including rectangular, non-flat, protruding teeth, more or less than two recesses, etc. In the example shown in FIG. 18, the corners do not have sharp angles. The corners are curved with a radius to act as stress relief and prevent damage to the tip. Forming two triangular shaped recesses directly opposite each other is also easy to make the recesses at a same time during manufacturing. A shape, such as shown in FIG. 14, is good for breaking a calculi having a relatively soft hardness. However, in order to break calculus with a relatively hard hardness, a protrusion such as teeth is better. With the shape shown in FIG. 18, a hybrid design is provided with substantially curved flat surfaces 132 (almost semi-circular) where the flat surfaces work best for softer targets, and the hybrid shape also comprises corners 134 which work better for harder targets. Thus, the tip 126 shown in FIG. 18 can be used for both hard and soft targets with a faster mass removal rate than a conventional flat shape. The shape also provides an atraumatic leading edge for the patient.

An example may be provided in an ultrasonic probe comprising a transducer; and a shaft configured to form a waveguide for directing ultrasonic waves, where a proximal end of the shaft is operatively connected to the transducer, where a distal end of the shaft is configured to direct ultrasonic waves toward a target, where the shaft comprises a conduit therethrough between the distal end and the proximal end, where the distal end of the shaft comprises a leading surface having a generally flat shape, where the distal end of the shaft further comprises a first recess, where the first recess terminates in at least one leading edge, the at least one leading edge forming a non-zero angle with the generally flat leading surface.

The distal end of the shaft may further comprise a second recess into the generally flat leading surface adjacent the entrance into the conduit, where the second recess forms terminates in a second at least one leading edge, the second at least one leading edge forming a non-zero angle with the generally flat leading surface. The second recess may be located diametrically opposed to the first recess. The generally flat leading surface may have a circular shape. The generally flat leading surface may have a general ring shape which is non-circular. The generally flat leading surface may form at least two teeth between the first and second recesses. The generally flat leading surface may form a majority of the surface along a front edge of the distal end of the shaft. The distal end of the shaft may form teeth at a front edge of the distal end of the shaft. The generally flat leading surface may have a generally rectangular shape. The generally flat leading surface may have a portion which is substantially semi-circular. The second recess may be located at a location which is not diametrically opposed to the first recess. The first recess may have a substantially triangular shape. The first recess may have a substantially rectangular shape. The first recess may have a substantially circular shape. Corners may be provided at locations where the first recess terminates in the at least one leading edge, and where the corners comprise angled corners having an angle of between about 100-160 degrees.

An example method can include providing a shaft configured to form a waveguide for directing ultrasonic waves, where the shaft comprises a proximal end, a distal end and a conduit therethrough between the distal end and the proximal end, where the distal end of the shaft comprises a leading surface having a generally flat shape; forming a first recess into the generally flat leading surface, where the first recess terminates in at least one leading edge, the leading edge of the first recess forming a non-zero angle with the generally flat leading surface; and connecting the proximal end of the shaft to a transducer, where the distal end of the shaft, at both the generally flat leading surface and one or more locations where the first recess terminates in the at least one leading edge, is configured to contact an anatomical target.

An example method can include inserting an ultrasonic probe into a body of a patient, where the ultrasonic probe comprises a shaft configured to form a waveguide for directing ultrasonic waves, where the shaft comprises a proximal end, a distal end and a conduit therethrough between the distal end and the proximal end; placing the distal end of the ultrasonic probe against an anatomical target, where the distal end of the shaft comprises a leading surface having a generally flat shape, where the distal end of the shaft further comprises a first recess into the generally flat leading surface, where the first recess terminates in at least one leading edge, the at least one leading edge of the first recess forming a non-zero angle with the generally flat leading surface; and vibrating the shaft to cause the distal end of the ultrasonic probe to vibrate against the anatomical target, where the distal end of the shaft, at both the generally flat leading surface and one or more locations where the first recess terminates in the at least one leading edge, contact the anatomical target during the vibration of the shaft to break at least a portion of the anatomical target.

An example method may be provided for inducing resonance in an anatomical target to thereby fragment the anatomical target, the method comprising: transmitting drive signals to drive a transducer of an ultrasonic probe; and vibrating a waveguide of the ultrasonic probe based upon the drive signals transmitted to the transducer, where the drive signals comprises a plurality of frequencies, at least one of the plurality of frequencies being a resonance frequency of the anatomical target such as to induce resonance in the anatomical target and thereby fragment the anatomical target.

The drive signals may be of variable frequency. The transducer can include a piezoelectric device, and where the transmitting of the drive signals comprises transmitting harmonic frequencies related to a fundamental frequency for resonance of the piezoelectric device. The transmitting of the drive signals drive signals can include a wave approximating a square wave, and where the multiple frequency drive signals cause an accelerated transition time in a shape change of a piezoelectric device. The ultrasonic waveguide can include a distal end which contacts the anatomical target and causes the resonance in the anatomical target.

An example may be provided with an apparatus comprising: an ultrasonic probe comprising a transducer and a waveguide for directing ultrasonic waves, where the waveguide comprises a distal end configured to contact an anatomical target; a driver configured to transmit drive signals to drive the transducer, where the drive signals comprises a plurality of frequencies, where at least one of the plurality of frequencies is a resonance frequency of the anatomical target such as to induce resonance in the anatomical target and thereby fragment the anatomical target.

An example may be provided with a non-transitory program storage device readable by a machine, tangibly embodying a program of instructions executable by the machine for performing operations, the operations comprising: transmitting drive signals by a driver to drive a transducer of an ultrasonic probe, where the transducer is configured to vibrate a waveguide of the ultrasonic probe based upon the drive signals transmitted to the transducer, and where the transmitting of the drive signals comprises transmitting the drive signals with a plurality of frequencies, where at least one of the plurality of frequencies is a resonance frequency of the anatomical target such as to induce resonance in the anatomical target and thereby fragment the anatomical target.

An example may be provided with an ultrasonic probe comprising: a transducer; and a shaft configured to form a waveguide for directing ultrasonic waves, where a proximal end of the shaft is connected to the transducer, where a distal end of the shaft is configured to contact an anatomical target where the shaft comprises a conduit therethrough between the distal end and the proximal end, where the distal end of the shaft is configured to form an ultrasonic horn.

The anatomical target may be a calculi, and where the distal end of the shaft is configured to contact the calculi. The transducer may be configured to generate an ultrasonic wave along a length of the shaft from the proximal end to the distal end, and where the ultrasonic horn is located after a last stationary stress node location in the shaft formed from the ultrasonic wave. The transducer may be configured to generate an ultrasonic wave along a length of the shaft from the proximal end to the distal end, and where the ultrasonic horn is located spaced from stationary stress node locations in the shaft formed from the ultrasonic wave. The ultrasonic probe may further comprise a second ultrasonic horn located proximate the transducer. The shaft, at the ultrasonic horn, may have a uniform outer diameter along a length of the ultrasonic horn. The shaft, at the ultrasonic horn, may have a uniform inner diameter along a length of the ultrasonic horn. The shaft, at the ultrasonic horn, may have a wall thickness which varies along a length of the ultrasonic horn. The ultrasonic horn may have a catenoidal shape. A cross sectional area of the shaft at the ultrasonic horn may be smaller than a cross sectional area of the shaft at another location of the shaft. The shaft can include a taper region in a transition zone between the ultrasonic horn and the rest of the shaft.

An example method may be provided comprising: providing a shaft configured to form a waveguide for directing ultrasonic waves, where the shaft comprises a proximal end, a distal end and a conduit therethrough between the distal end and the proximal end, where the distal end of the shaft is configured to form an ultrasonic horn; and connecting the proximal end of the shaft to a transducer.

An example method may be provided comprising: inserting an ultrasonic probe into a body of a patient, where the ultrasonic probe comprises a shaft configured to form a waveguide for directing ultrasonic waves, where the shaft comprises a proximal end, a distal end and a conduit therethrough between the distal end and the proximal end, and where the distal end of the shaft is configured to form an ultrasonic horn; placing the distal end of the ultrasonic probe against anatomical target inside the patient; and vibrating the shaft by a transducer to cause the distal end of the ultrasonic probe to vibrate against the anatomical target, where the ultrasonic horn at the distal end of the shaft increases displacement of the distal end of the shaft at the anatomical target. The ultrasonic horn at the distal end of the shaft may be located spaced from stationary stress node locations in the shaft formed from an ultrasonic wave from the transducer.

An example may be provided with an ultrasonic probe comprising: a transducer; and a shaft configured to form an ultrasonic waveguide, where a proximal end of the shaft is connected to the transducer, where a distal end of the shaft is configured to contact a calculi, where the shaft comprises a conduit therethrough between the distal end and the proximal end, where the distal end of the shaft comprises a leading surface having a substantially flat shape, where the distal end of the shaft further comprises a first recess into the substantially flat leading surface adjacent an entrance into the conduit, where the first recess forms two corners at junctions of the first recess with the substantially flat leading surface.

The distal end of the shaft may further comprise a second recess into the substantially flat leading surface adjacent the entrance into the conduit, where the second recess forms two corners at junctions of the second recess with the substantially flat leading surface. The second recess may be located diametrically opposed to the first recess. The first recess may have a substantially triangular shape. The corners may be angled corners having an angle of between about 100-160 degrees.

An example method may be provided comprising: providing a shaft configured to form an ultrasonic waveguide, where the shaft comprises a proximal end, a distal end and a conduit therethrough between the distal end and the proximal end, where the distal end of the shaft comprises a leading surface having a substantially flat shape; forming a first recess into the substantially flat leading surface adjacent an entrance into the conduit, where the first recess forms two corners at junctions of the first recess with the substantially flat leading surface; and connecting the proximal end of the shaft to a transducer, where the distal end of the shaft, at both the substantially flat leading surface and the two corners at the junctions with the first recess, is configured to contact a calculi.

An example method may be provided comprising: inserting an ultrasonic probe into a body of a patient, where the ultrasonic probe comprises a shaft configured to form an ultrasonic waveguide, where the shaft comprises a proximal end, a distal end and a conduit therethrough between the distal end and the proximal end; placing the distal end of the ultrasonic probe against a calculi inside the patient, where the distal end of the shaft comprises a leading surface having a substantially flat shape, where the distal end of the shaft further comprises a first recess into the substantially flat leading surface adjacent an entrance into the conduit, where the first recess forms two corners at junctions of the first recess with the substantially flat leading surface; and vibrating the shaft to cause the distal end of the ultrasonic probe to vibrate against the calculi, where the distal end of the shaft, at both the substantially flat leading surface and the two corners at the junctions with the first recess, contact a calculi during the vibration of the shaft to break at least a portion of the calculi.

An example method may be provided comprising: transmitting drive signals to a transducer of an ultrasonic probe; and vibrating an ultrasonic waveguide of the ultrasonic probe based upon the drive signal transmitted to the transducer, where the drive signals comprises multiple frequencies to cause the transducer to vibrate the ultrasonic waveguide with an increased likelihood of the ultrasonic waveguide exciting a resonance frequency of a calculi contacting the ultrasonic waveguide.

The transmitting of the drive signals drive signals can include a wave approximating a square wave. The transmitting of the drive signals can include frequency sweeping. The transducer can include a piezoelectric device, and the transmitting of the drive signals can include transmitting harmonic frequencies related to a fundamental frequency for resonance of the piezoelectric device. The multiple frequency drive signals may cause an accelerated transition time in a shape change of the piezoelectric device. The ultrasonic waveguide can include a distal end which contacts the calculi and causes the resonance in the calculi.

An example may be provided with an apparatus comprising: an ultrasonic probe comprising a transducer and an ultrasonic waveguide, where the ultrasonic waveguide comprises a distal end configured to contact a calculi; a driver configured to transmit drive signals to the transducer, where the drive signals comprises multiple frequencies to cause the transducer to vibrate the ultrasonic waveguide with an increased likelihood of the ultrasonic waveguide exciting a resonance frequency of the calculi contacting the ultrasonic waveguide.

An example may be provided with a non-transitory program storage device readable by a machine, tangibly embodying a program of instructions executable by the machine for performing operations, the operations comprising: transmitting drive signals by a driver to a transducer of an ultrasonic probe, where the transducer is configured to vibrate the ultrasonic waveguide based upon the drive signals transmitted to the transducer, and where the transmitting of the drive signals comprises transmitting the drive signals with multiple frequencies to cause the transducer to vibrate the ultrasonic waveguide with an increased likelihood of the ultrasonic waveguide exciting a resonance frequency of a calculi contacting the ultrasonic waveguide.

An example may be provided with an ultrasonic probe comprising: a transducer; and a shaft configured to form an ultrasonic waveguide, where a proximal end of the shaft is connected to the transducer, where a distal end of the shaft is configured to contact a calculi, where the shaft comprises a conduit therethrough between the distal end and the proximal end, where the distal end of the shaft comprises an ultrasonic horn.

The transducer may be configured to generate an ultrasonic wave along a length of the shaft from the proximal end to the distal end, and the ultrasonic horn may be located after a last stationary stress node location in the shaft formed from the ultrasonic wave. The transducer may be configured to generate an ultrasonic wave along a length of the shaft from the proximal end to the distal end, and the ultrasonic horn may be located spaced from stationary stress node locations in the shaft formed from the ultrasonic wave. The ultrasonic probe may further comprise a second ultrasonic horn located proximate the transducer. The shaft, at the ultrasonic horn, may have a uniform outer diameter along a length of the ultrasonic horn. The shaft, at the ultrasonic horn, may have a uniform inner diameter along a length of the ultrasonic horn. The shaft, at the ultrasonic horn, may have a wall thickness which varies along a length of the ultrasonic horn. The ultrasonic horn may have a catenoidal shape. A cross sectional area of the shaft at the ultrasonic horn may be smaller than a cross sectional area of the shaft at another location of the shaft. The shaft can include a taper region in a transition zone between the ultrasonic horn and the rest of the shaft.

An example method may be provided comprising: providing a shaft configured to form an ultrasonic waveguide, where the shaft comprises a proximal end, a distal end and a conduit therethrough between the distal end and the proximal end, where the distal end of the shaft comprises an ultrasonic horn; and connecting the proximal end of the shaft to a transducer.

An example method may be provided comprising: inserting an ultrasonic probe into a body of a patient, where the ultrasonic probe comprises a shaft configured to form an ultrasonic waveguide, where the shaft comprises a proximal end, a distal end and a conduit therethrough between the distal end and the proximal end, and where the distal end of the shaft comprises an ultrasonic horn: placing the distal end of the ultrasonic probe against a calculi inside the patient; and vibrating the shaft by a transducer to cause the distal end of the ultrasonic probe to vibrate against the calculi, where the ultrasonic horn at the distal end of the shaft increases displacement of the distal end of the shaft at the calculi. The ultrasonic horn at the distal end of the shaft may be located spaced from stationary stress node locations in the shaft formed from an ultrasonic wave from the transducer.

It should be understood that the above description is only illustrative. Various alternatives and modifications can be devised by those skilled in the art. For example, features recited in the various dependent claims could be combined with each other in any suitable combination(s). In addition, features from different examples described above could be selectively combined into a new example. Accordingly, the description is intended to embrace all such alternatives, modifications and variances which fall within the scope of the appended claims.

VARIOUS NOTES & EXAMPLES

Each of these non-limiting examples can stand on its own, or can be combined in various permutations or combinations with one or more of the other examples.

Example 1 can include an apparatus for treating a calculus mass with an acoustic probe comprising an acoustic transducer. The apparatus can include controller circuitry configured for providing a plurality of drive signal components corresponding to a plurality of frequencies, to produce an acoustic resonance frequency of the acoustic probe that is targeted to the calculus mass and an output interface configured for communicating the plurality of drive signal components to the acoustic transducer to produce the targeted acoustic resonance frequency.

Example 2 can include Example 1, wherein the acoustic transducer comprises one or more piezoelectric members configured to receive the plurality of drive signal components from the controller circuitry and to convert the plurality of drive signal components into acoustic energy.

Example 3 can include any of Examples 1-2, further comprising a waveguide extending distally from the acoustic transducer, the waveguide configured to propagate a waveform based on the targeted acoustic resonance frequency.

Example 4 can include any of Examples 1-3, further comprising a probe tip distal of the acoustic transducer, the probe tip longitudinally displaceable using the propagated waveform to fracture the calculus mass.

Example 5 can include an apparatus for treating a calculus mass an acoustic probe. The apparatus can include an acoustic probe comprising an acoustic transducer, and an input interface configured to receive, from controller circuitry, a plurality of drive signal components corresponding to a plurality of frequencies, to produce an acoustic resonance frequency of the acoustic probe that is targeted to the calculus mass.

Example 6 can include Example 5, wherein the acoustic transducer comprises one or more piezoelectric members configured to receive the plurality of drive signal components from the controller circuitry and convert the plurality of drive signal components into acoustic energy.

Example 7 can include any of Examples 5-6, further comprising a waveguide extending distally from the acoustic transducer, the waveguide configured to propagate a waveform based on the targeted acoustic resonance frequency.

Example 8 can include any of Examples 5-7, further comprising a probe tip distal of the acoustic transducer, the probe tip longitudinally displaceable by the waveform to fracture a calculus mass.

Example 9 can include a method of fracturing a calculus mass with an acoustic probe comprising an acoustic transducer. The method can include providing or receiving a plurality of drive signal components corresponding to a plurality of frequencies, to produce an acoustic resonance frequency of the acoustic probe that is targeted to the calculus mass, and communicating the plurality of drive signal components to the acoustic transducer to produce the targeted acoustic resonance frequency.

Example 10 can include Example 9, wherein the plurality of drive signal components correspond to a plurality of frequencies, and wherein superpositioning of the plurality of drive signal components results in the targeted acoustic resonance frequency.

Example 11 can include any of Examples 9-10, wherein the plurality of drive signal components correspond to a plurality of frequencies, and at least one of the plurality of frequencies is the targeted acoustic resonance frequency.

Example 12 can include any of Examples 9-11, wherein the plurality of frequencies comprises a sweep of frequencies including the acoustic resonance frequency.

Example 13 can include any of Examples 9-12, wherein at least one of the plurality of frequencies comprises a harmonic frequency of a fundamental frequency for resonance of the acoustic probe.

Example 14 can include any of Examples 9-13, wherein the harmonic frequency comprises an odd harmonic.

Example 15 can include any of Examples 9-14, wherein the harmonic frequency comprises a third harmonic frequency or a fifth harmonic frequency.

Example 16 can include any of Examples 9-15, wherein plurality of drive signal components combine to comprise a wave approximating a square wave.

Example 17 can include any of Examples 9-16, wherein at least one of the plurality of drive signal components cause an accelerated transition time in a shape change of a piezoelectric device in the acoustic transducer.

Example 18 can include any of Examples 9-17, further comprising producing a waveform based on the sum of the plurality of drive signal components.

Example 19 can include any of Examples 9-18, further comprising identifying a fundamental frequency based upon an acoustic resonance frequency of the calculus mass, and selecting the plurality of drive signal components based on the fundamental frequency.

Example 20 can include any of Examples 9-19, wherein each of the plurality of drive signal components corresponds to a different one of the plurality of frequencies.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific examples in which the present devices or techniques can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure, it is submitted with the understanding that it will not be used to interpret or limit the scope or meaning of the claims. Also, in the above Detailed Description, various features may be grouped together to streamline the disclosure. The following claims are hereby incorporated into the Detailed Description as examples or embodiments, with each claim standing on its own as a separate embodiment, and it is contemplated that such embodiments can be combined with each other in various combinations or permutations. The scope of the present devices or techniques should be determined with reference to the appended claims, along with the full scope of equivalents to which such claims are entitled.

What is claimed is:

1. An apparatus for treating a calculus mass with an acoustic probe comprising an acoustic transducer, the apparatus comprising:
    a controller circuitry configured for providing a plurality of drive signal components corresponding to a plurality of frequencies, to produce an acoustic resonance frequency of the acoustic probe that is targeted to the calculus mass;
    an output interface configured for communicating the plurality of drive signal components to the acoustic transducer to produce the acoustic resonance frequency;
    an acoustic waveguide extending distally from the acoustic transducer, the acoustic waveguide configured to propagate an acoustic waveform based on the acoustic resonance frequency produced based on the plurality of frequencies; and
    a probe tip distal of the acoustic transducer, the probe tip longitudinally displaceable using the propagated acoustic waveform to fracture the calculus mass.

2. The apparatus of claim 1, wherein the acoustic transducer comprises one or more piezoelectric members configured to receive the plurality of drive signal components from the controller circuitry and to convert the plurality of drive signal components into acoustic energy.

3. The apparatus of claim 1, wherein the probe tips is integral with the acoustic waveguide.

4. An apparatus for treating a calculus mass with an acoustic probe, the apparatus comprising:
    the acoustic probe comprising an acoustic transducer;
    an input interface configured to receive, from a controller circuitry, a plurality of drive signal components corresponding to a plurality of frequencies, to produce an acoustic resonance frequency of the acoustic probe that is targeted to the calculus mass;
    further comprising an acoustic waveguide extending distally from the acoustic transducer, the acoustic waveguide configured to propagate an acoustic waveform based on the targeted acoustic resonance frequency; and
    a probe tip distal of the acoustic transducer, the probe tip longitudinally displaceable by the propagated acoustic waveform to fracture a calculus mass.

5. The apparatus of claim 4, wherein the acoustic transducer comprises one or more piezoelectric members configured to receive the plurality of drive signal components from the controller circuitry and convert the plurality of drive signal components into acoustic energy.

6. The apparatus of claim 4, wherein the probe tips is integral with the acoustic waveguide.

7. A method of fracturing a calculus mass with an acoustic probe comprising an acoustic transducer, the method comprising:
    providing or receiving a plurality of drive signal components corresponding to a plurality of frequencies, to produce an acoustic resonance frequency of the acoustic probe that is targeted to the calculus mass;

communicating the plurality of drive signal components to the acoustic transducer to produce the acoustic resonance frequency; and producing a waveform based on the plurality of frequencies, wherein at least one of the plurality of frequencies comprises a harmonic frequency of a fundamental frequency for resonance of the acoustic probe.

8. The method of claim 7, wherein the plurality of drive signal components correspond to a plurality of frequencies, and wherein superpositioning of the plurality of drive signal components results in the targeted acoustic resonance frequency.

9. The method of claim 7, wherein the plurality of drive signal components correspond to the plurality of frequencies, and at least one of the plurality of frequencies is the targeted acoustic resonance frequency.

10. The method of claim 7, wherein the plurality of frequencies comprises a sweep of frequencies including the acoustic resonance frequency.

11. The method of claim 7, wherein the harmonic frequency comprises an odd harmonic.

12. The method of claim 11, wherein the harmonic frequency comprises a third harmonic frequency or a fifth harmonic frequency.

13. The method of claim 7, wherein the plurality of drive signal components combine to comprise a wave approximating a square wave.

14. The method of claim 7, wherein at least one of the plurality of drive signal components causes an accelerated transition time in a shape change of a piezoelectric device in the acoustic transducer.

15. The method of claim 7, further comprising producing a waveform based on a sum of the plurality of drive signal components.

16. The method of claim 7, further comprising identifying a fundamental frequency based upon an acoustic resonance frequency of the calculus mass, and selecting the plurality of drive signal components based on the fundamental frequency.

17. The method of claim 7, wherein each of the plurality of drive signal components corresponds to a different one of the plurality of frequencies.

\* \* \* \* \*

UNITED STATES PATENT AND TRADEMARK OFFICE
CERTIFICATE OF CORRECTION

| | | |
|---|---|---|
| PATENT NO. | : 11,759,220 B2 | Page 1 of 1 |
| APPLICATION NO. | : 17/037072 | |
| DATED | : September 19, 2023 | |
| INVENTOR(S) | : Baker et al. | |

It is certified that error appears in the above-identified patent and that said Letters Patent is hereby corrected as shown below:

On the Title Page

In item (71), in "Applicant", in Column 1, Line 1, delete "AMCI," and insert --ACMI,-- therefor Signed and Sealed this
Fifteenth Day of April, 2025

Coke Morgan Stewart
*Acting Director of the United States Patent and Trademark Office*